(12) United States Patent
Tavassoli

(10) Patent No.: US 10,962,549 B2
(45) Date of Patent: Mar. 30, 2021

(54) HIF-1 AND HIF-2 INHIBITORS

(71) Applicant: University of Southampton, Southampton (GB)

(72) Inventor: Ali Tavassoli, Southampton (GB)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 0 days.

(21) Appl. No.: 16/072,803

(22) PCT Filed: Jan. 27, 2017

(86) PCT No.: PCT/GB2017/050220
§ 371 (c)(1),
(2) Date: Jul. 25, 2018

(87) PCT Pub. No.: WO2017/129997
PCT Pub. Date: Aug. 3, 2017

(65) Prior Publication Data
US 2019/0033318 A1    Jan. 31, 2019

(30) Foreign Application Priority Data

Jan. 27, 2016  (GB) .................................... 1601527

(51) Int. Cl.
| | | |
|---|---|---|
| *A61K 38/18* | (2006.01) | |
| *A61K 38/08* | (2019.01) | |
| *A61P 35/00* | (2006.01) | |
| *C07K 14/47* | (2006.01) | |
| *C07K 7/06* | (2006.01) | |
| *C07K 7/02* | (2006.01) | |
| *G01N 33/68* | (2006.01) | |

(52) U.S. Cl.
CPC ......... *G01N 33/6845* (2013.01); *A61K 38/08* (2013.01); *A61K 38/18* (2013.01); *A61P 35/00* (2018.01); *C07K 7/02* (2013.01); *C07K 7/06* (2013.01); *C07K 14/4702* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 6,020,462 A | 2/2000 | Semenza | |
| 2009/0098127 A1* | 4/2009 | Mabjeesh | A61K 38/1709 514/1.1 |
| 2013/0210749 A1* | 8/2013 | Krissansen | C07K 14/005 514/21.5 |

FOREIGN PATENT DOCUMENTS

| | | |
|---|---|---|
| WO | WO2011078351 A1 | 5/2013 |
| WO | WO2014078479 | 5/2014 |
| WO | WO2014165277 | 10/2014 |

OTHER PUBLICATIONS

Atopobium vaginae DSM 15829 protein, UniProtKB Accession No. F1T669, accessed Nov. 11, 2019 at URL: uniprot.org/uniprot/F1T669, pp. 1-3 (Year: 2019).*
Tolypothrix sp. PCC 7601 protein, UniProtKB Accession No. A0A0D6KS78, accessed Nov. 11, 2019 at URL: uniprot.org/uniprot/A0A0D6KS78, pp. 1-3 (Year: 2019).*
Arundo donax protein, UniProtKB Accession No. A0A0A9J6E5, accessed Nov. 11, 2019 at URL: uniprot.org/uniprot/A0A0A9J6E5, pp. 1-3 (Year: 2019).*
Perabo et al., "Soy isoflavone genistein in prevention and treatment of prostate cancer," Prostate Cancer and Prostatic Diseases 11 :6-12 (2008) (Year: 2008).*
Lesiak et al., Blocking angiogenesis with peptides that inhibit the activity of procollagen C-endopeptidase, Pharmacol. Rep. 61:468-476 (2009) (Year: 2009).*
Real et al., "Antiviral Drug Discovery Strategy Using Combinatorial Libraries of Structurally Constrained Peptides," J. Virol. 78:7410-7417 (2004) (Year: 2004).*
International Prelimianry Report on Patentability dated Aug. 9, 2018 in International Application PCT/GB2017/050220, 14 pages.
Cardoso et al., "Identification of Cys255 in HIF-1 alpha as a novel site for development of covalent inhibitors of HIF-1 alpha/ARNT PasB domain protein—protein interaction," Oct. 2012. Protein Science, 21(12):1885-1896.
GB Search Report for Application No. GB 1601527.3, dated Oct. 2016, 5 pages.
PCT Search Report & Written Opinion for Application No. PCT/GB2017/050220, dated May 22, 2017, 19 pages.
Milroy et al., "Modulators of protein-protein interactions," May 2014. Chemical Reviews, 114(9): 4695-4748.
Miranda et al., "A cyclic peptide inhibitor of HIF-1 heterodimerization that inhibits hypoxia signaling in cancer cells," Jun. 2013. Journal of the American Chemical Society, 135 (28): 10418-10425.
Wang et al., "A cell-penetrating peptide suppresses the hypoxia inducible fator-1 function by binding to the helix-loop-helix domain of the aryl hydrocarbon receptor nuclear translocator," Apr. 2013. Chemico-Biological Interactions, Elsevier Science Ireland, 203(2):401-411.

* cited by examiner

*Primary Examiner* — Julie Ha
*Assistant Examiner* — Kristina M Hellman
(74) *Attorney, Agent, or Firm* — Parker Highlander PLLC

(57) ABSTRACT

The present invention relates to inhibitors of HIF-1 and HIF-2 and uses thereof. The present invention further relates to the inhibitors for use in treatment of diseases. An isolated polypeptide is provided, that prevents dimerization of HIF-1α with HIF-1β and HIF-2α with HIF-1β and/or inhibits the activity of HIF-1 and HIF-2, wherein the polypeptide comprises the amino acid sequence C-X1-X2-X3-Z-X4 (SEQ ID NO 1) and wherein X1, X2, X3 and X4 are any amino acid and wherein Z is leucine, valine of isoleucine or a non-natural derivative or leucine, valine or isoleucine. The isolated polypeptide prevents dimerization of HIF-1α with HIF-1β and HIF-2α with HIF-1β and inhibits the activity of HIF-1 and HIF-2 by binding to HIF-1α or HIF-1β and/or HIF-2α or HIF-1β.

9 Claims, 16 Drawing Sheets
Specification includes a Sequence Listing.

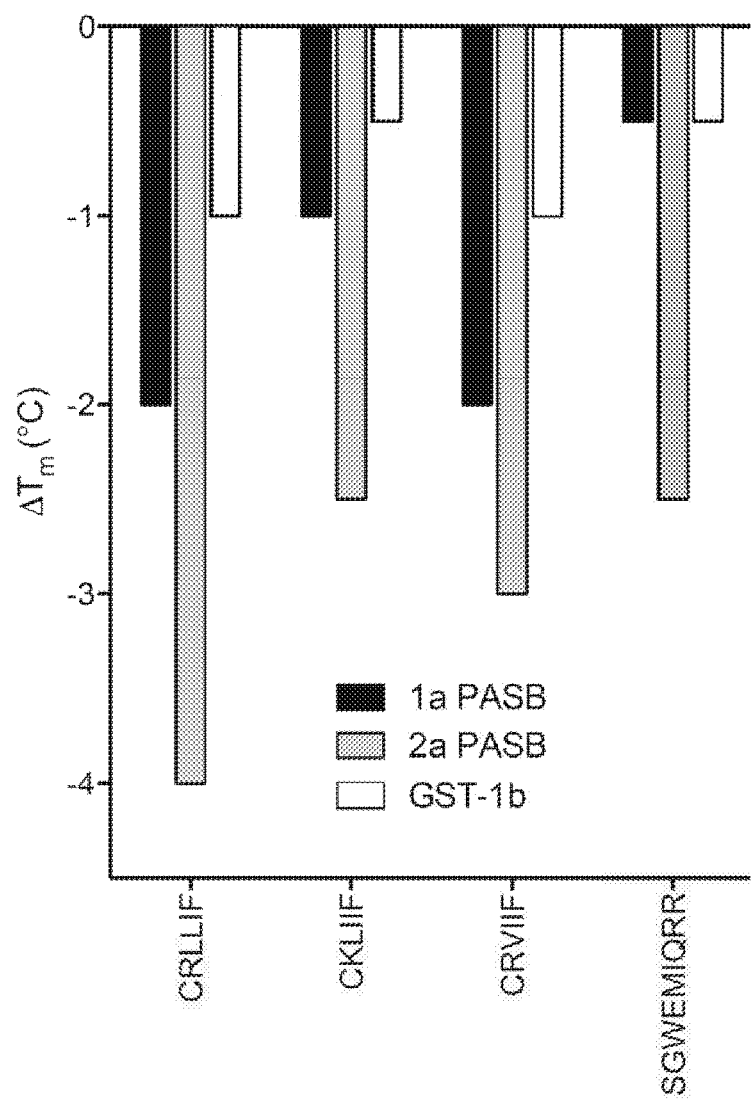
Figure 1. Thermal shift assay of inhibitors.

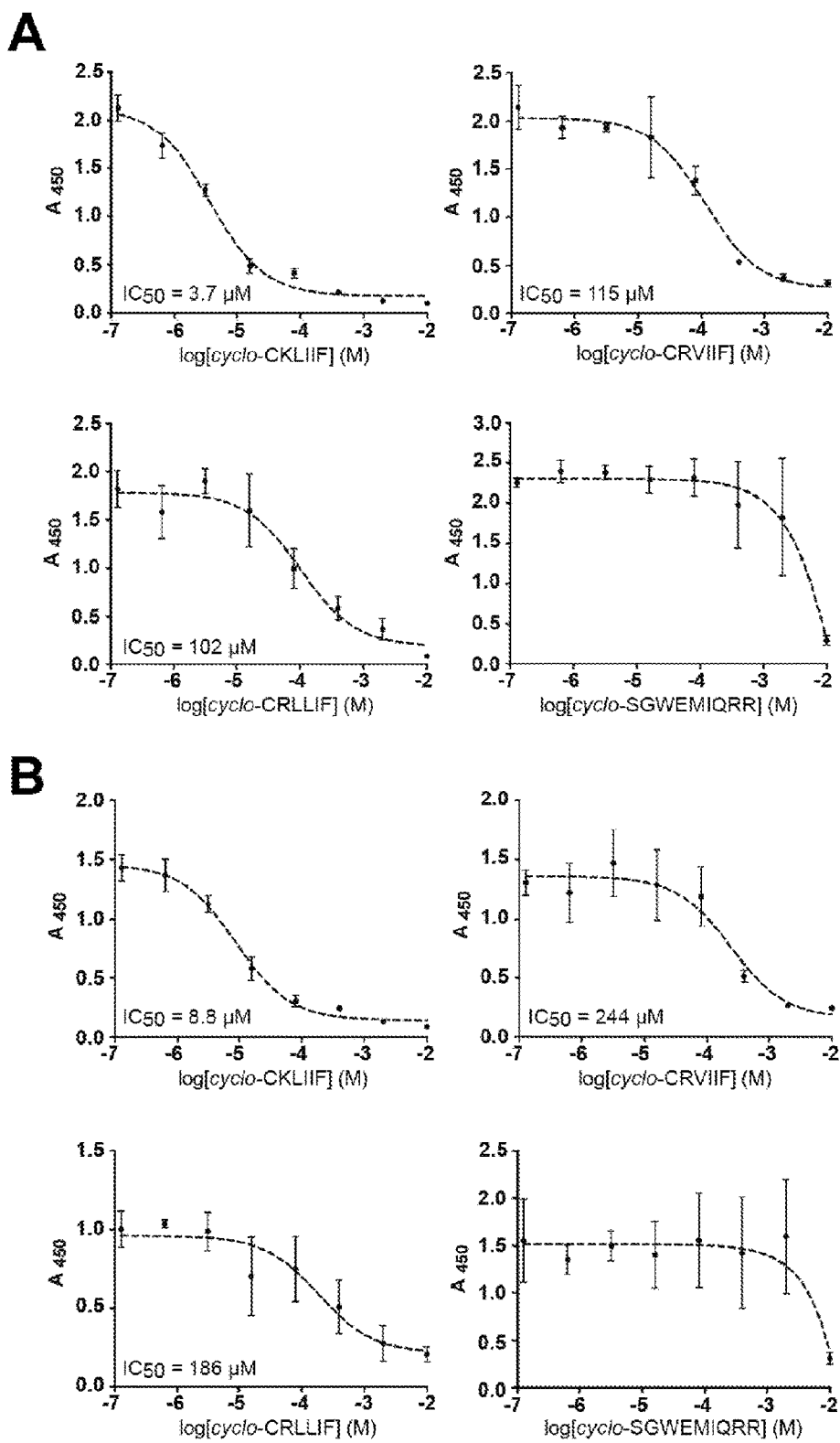
Figures 2A-2B. ELISA analysis of inhibitor activity. A) inhibitors were assayed for ability to disrupt the HIF-1α/HIF-1β protein-protein interaction. B) inhibitors were assayed for ability to disrupt the HIF-2α/HIF-1β protein-protein interaction

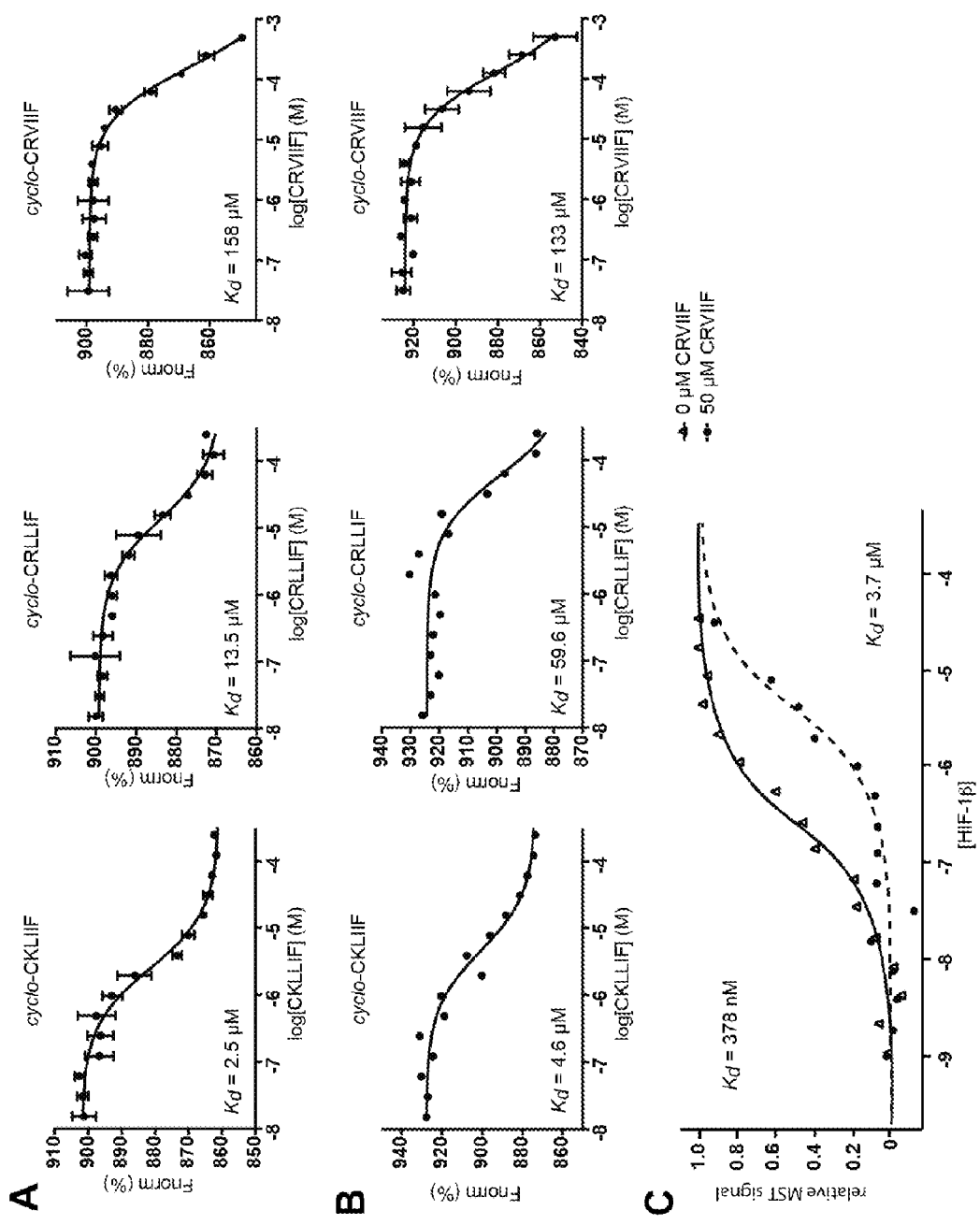
Figures 3A-3C. MST analysis of the binding of the inhibitors to the PASB domain of A) HIF-1α and B) HIF-2α. C) The $K_d$ of the HIF-1α/HIF-1β protein-protein interaction increases in the presence of 50 μM CRVIIF.

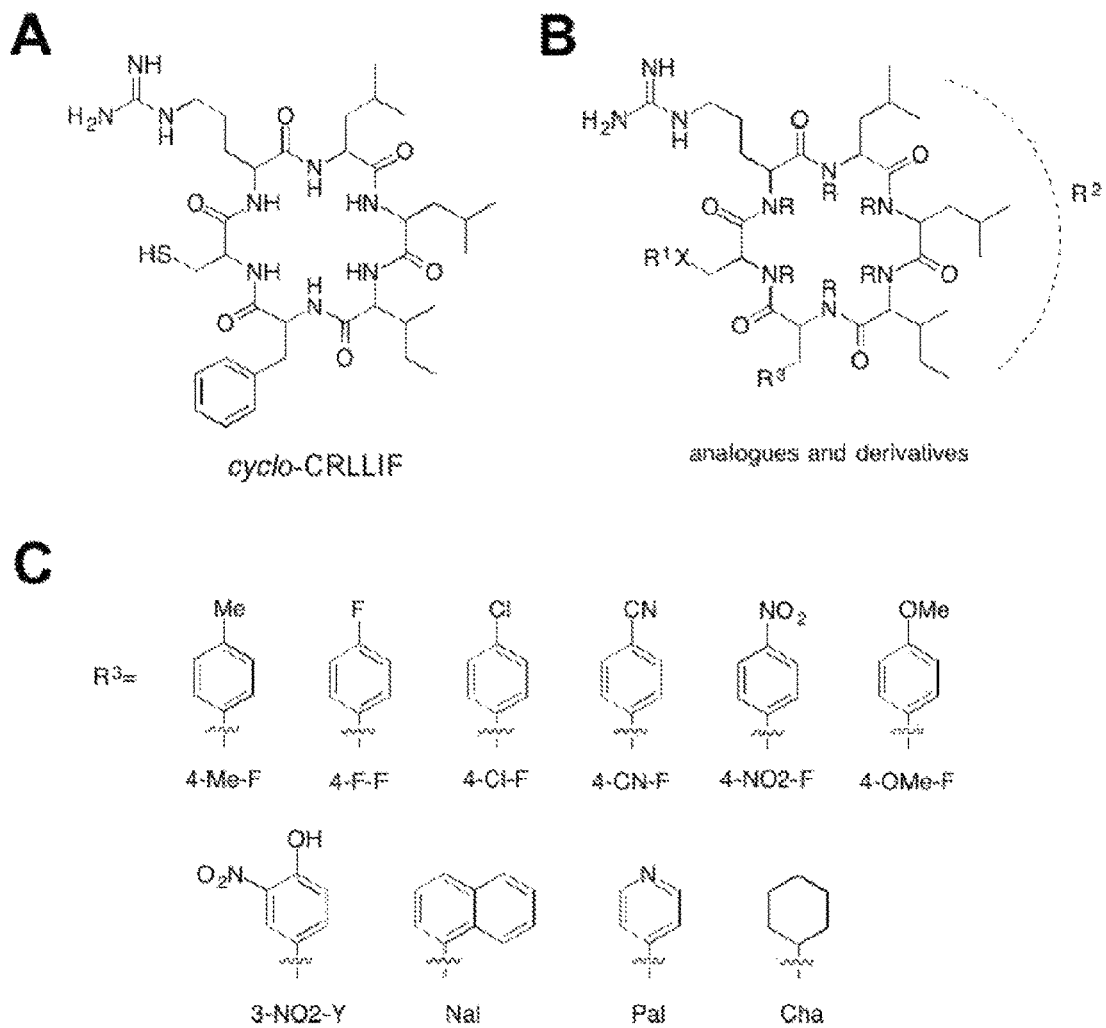

Figures 4A-4C. A) Structure of *cyclo*-CRLLIF. B) Potential sites for generation of analogues. X = atom, e.g. S or O; R and $R^1$ = any atom or functional group, e.g. H, Me, Et; $R^2$ = replacement of the LLI motif with any combination of aliphatic amino acids (natural or non-natural) e.g. valine, leucine, homoleucine, isoleucine. $R^3$= any substituted phenyl, cyclohexyl, naphthyl, pyridyl, or other ring. Amino acids may be L or D in any or all positions, as well as the reverse sequence. The arginine may be replaced with lysine, ornithine or other nitrogen containing non-natural amino acids. C) The derivatives generated in this study.

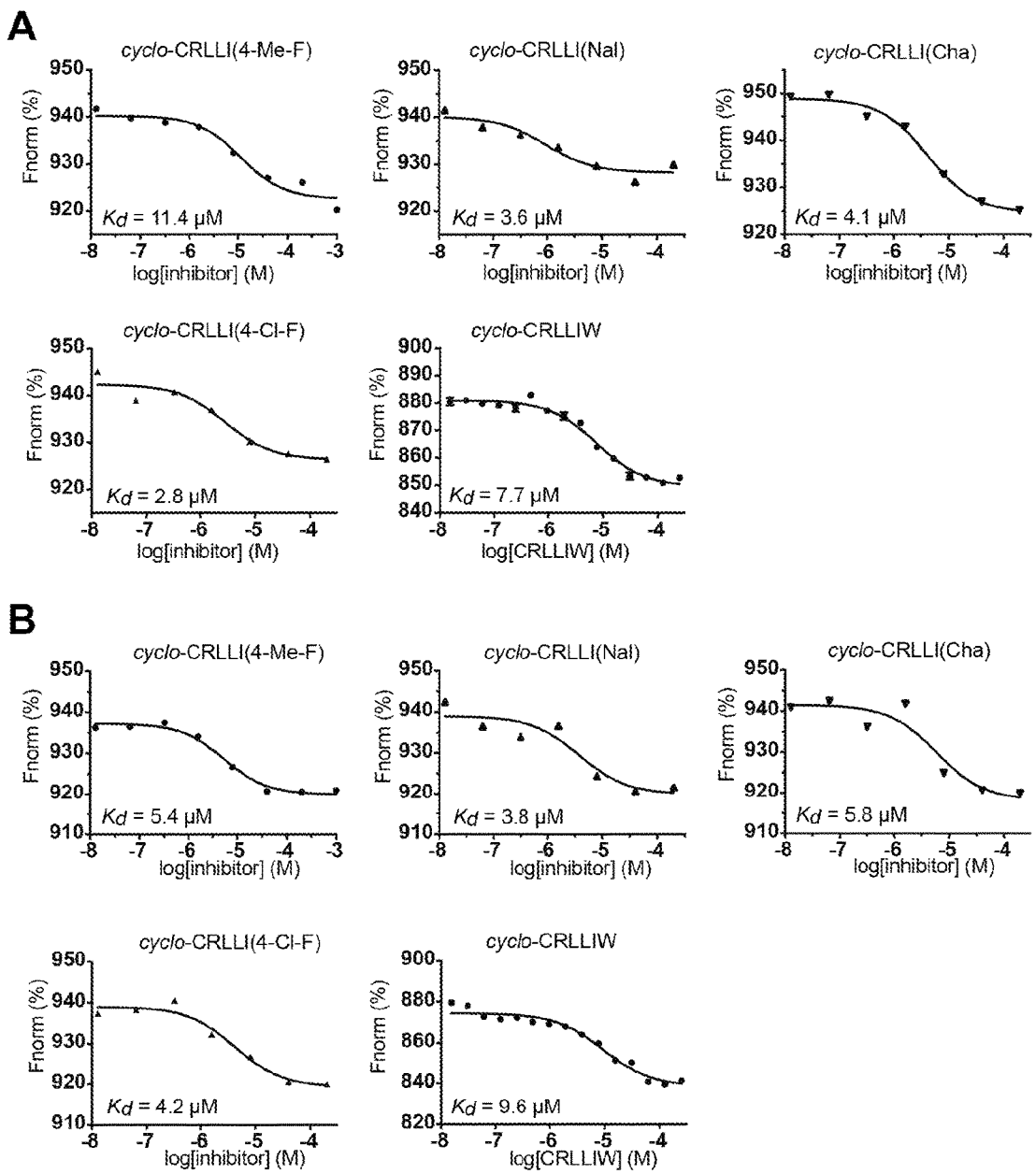
Figures 5A-5B. MST analysis of derivatives of CRLLIF. For full list of analogues and their activity, see Table 4. A) Binding affinity of given derivative for the PAS-B domain of HIF-1α. B) Binding affinity of given derivative for the PAS-B domain of HIF-2α.

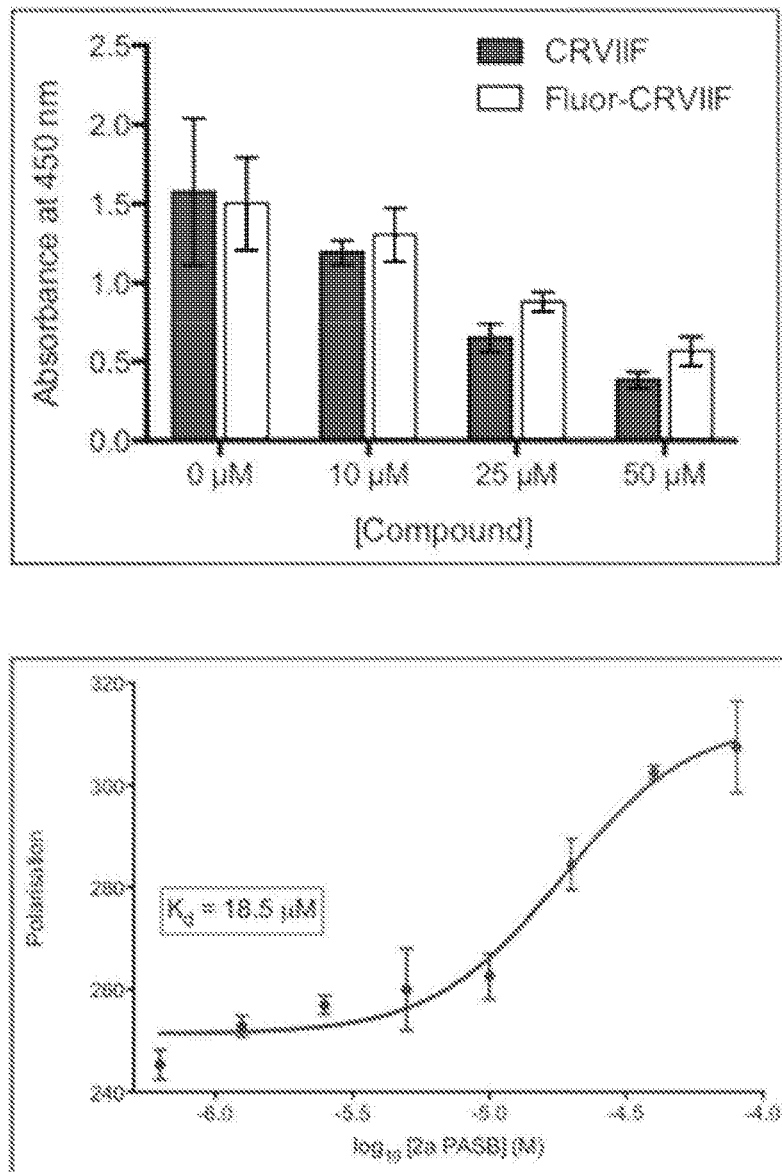
Figure 6. Analysis of binding of fluor-CRVIIF to the PAS-B domain of HIF-2α by ELISA (upper panel) and Fluorescence polarization (lower panel).

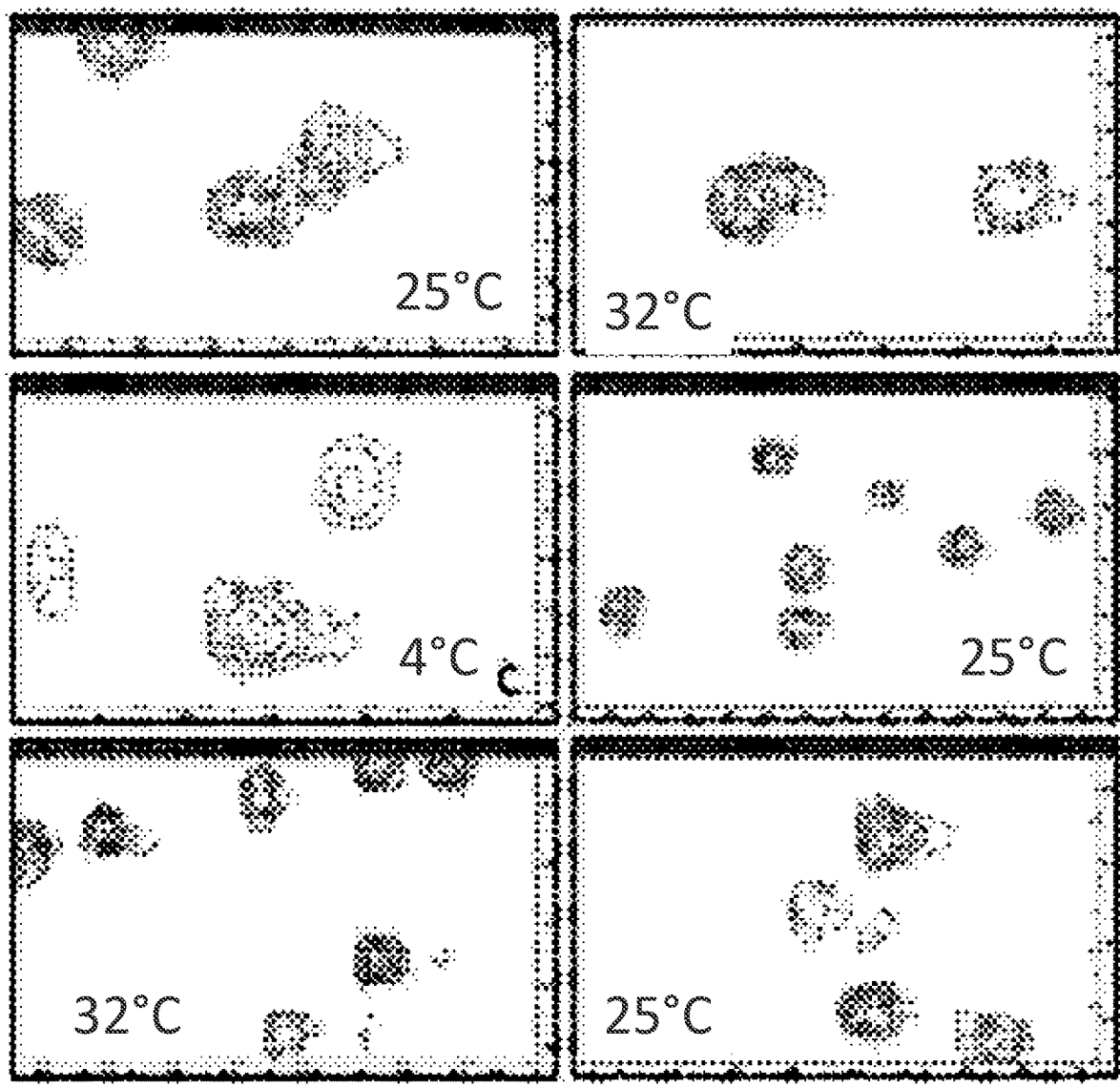
Figure 7A. N15 NMR analysis of the binding of CRVIIF to the PAS-B domain of HIF-2a

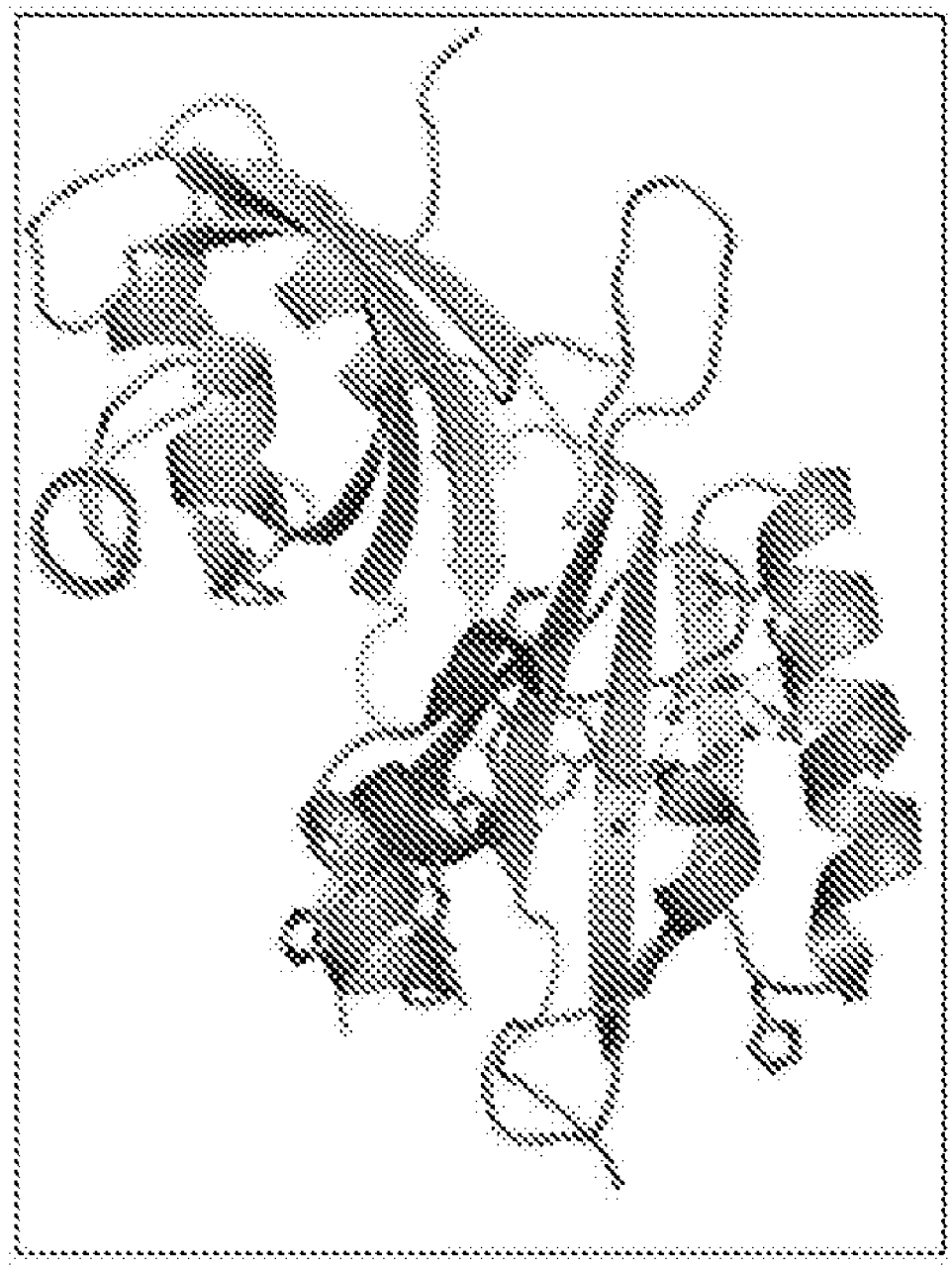
Figure 7B. $N^{15}$ NMR analysis of the binding of CRVIIF to the PAS-B domain of HIF-2a Figure 8. Proposed binding site of CRVIIF to the PAS-B domain of Hif1α and Hif2α

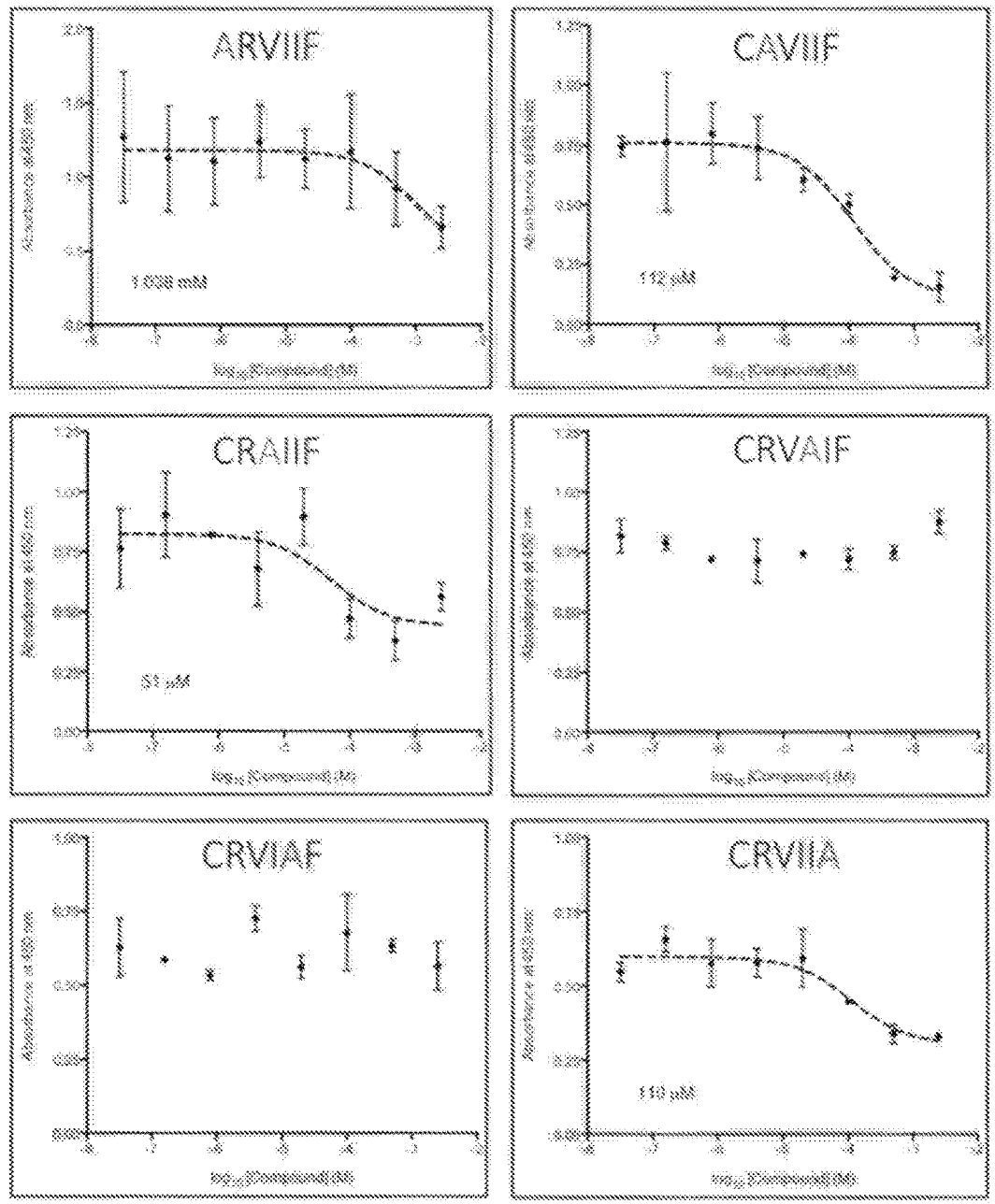
Figure 9A. Assessing the importance of each residue of CRVIIF for its activity (assessed by HIF-1α/HIF-1β ELISA) by alanine scanning. A similar approach may be used to identify the active residues in the other cyclic peptides reported here.

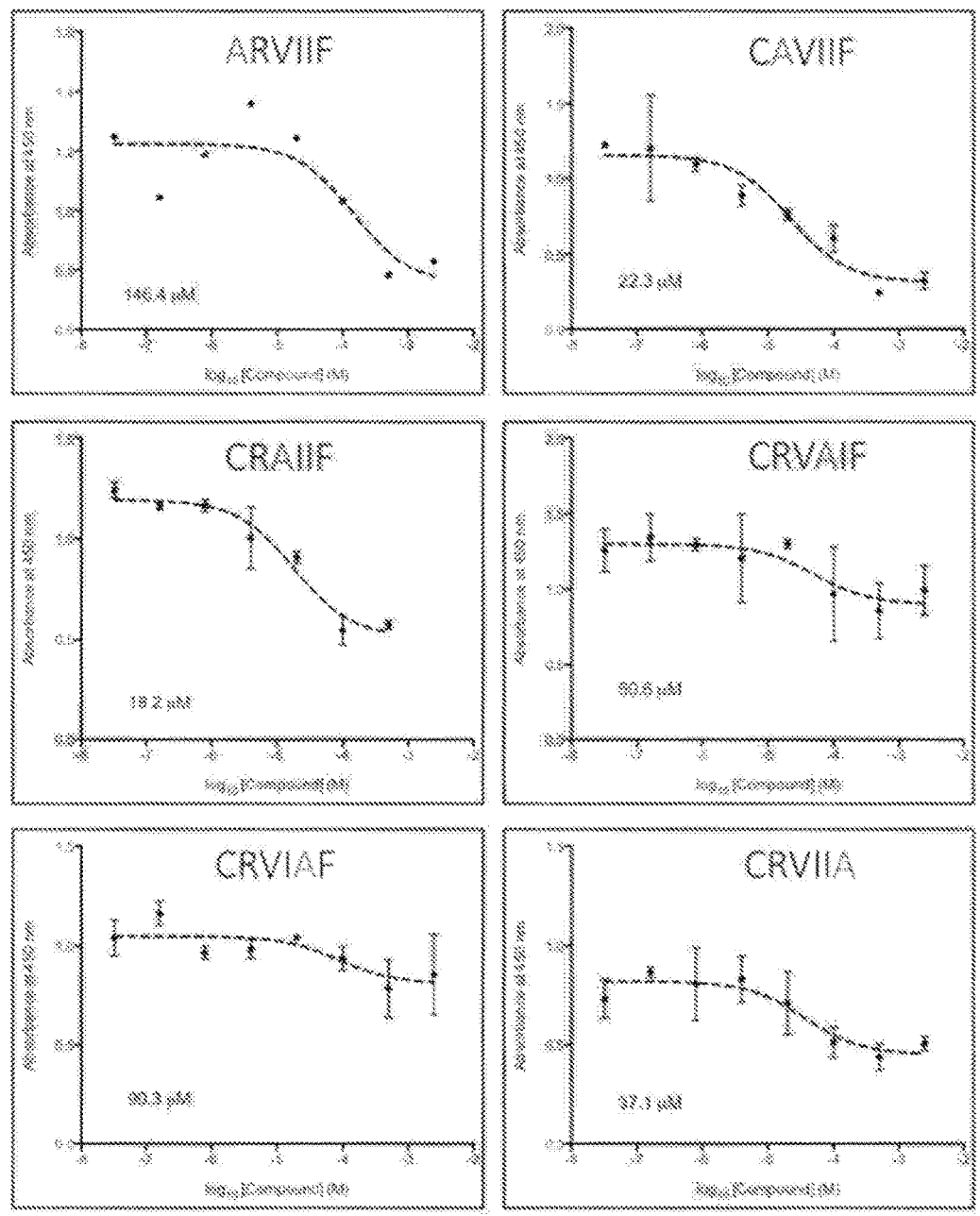
Figure 9B. Assessing the importance of each residue of CRVIIF for its activity (assessed by HIF-2α/HIF-1β ELISA) by alanine scanning. A similar approach may be used to identify the active residues in the other cyclic peptides reported here.

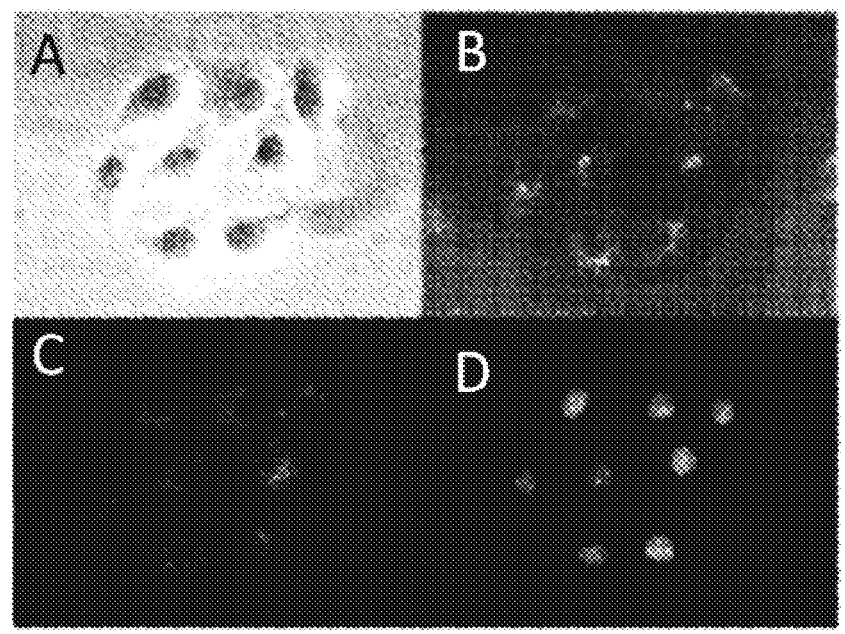
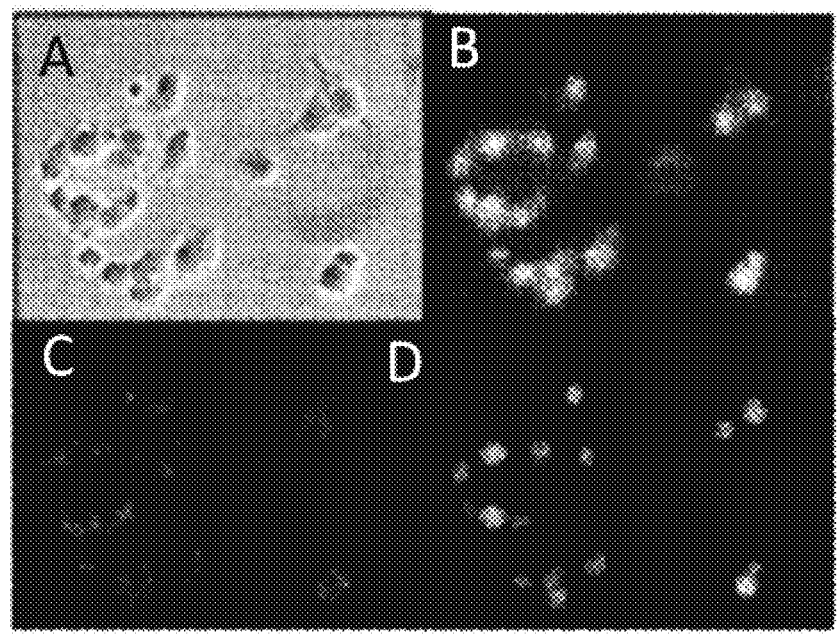
Figure 10 – Assessing the cell permeability of fluor-CRVIIF by microscopy. White areas in panels B show fluorescently labelled CRVIIF; white areas in panels C show vesicles; and white areas in panels D show the nuclei.

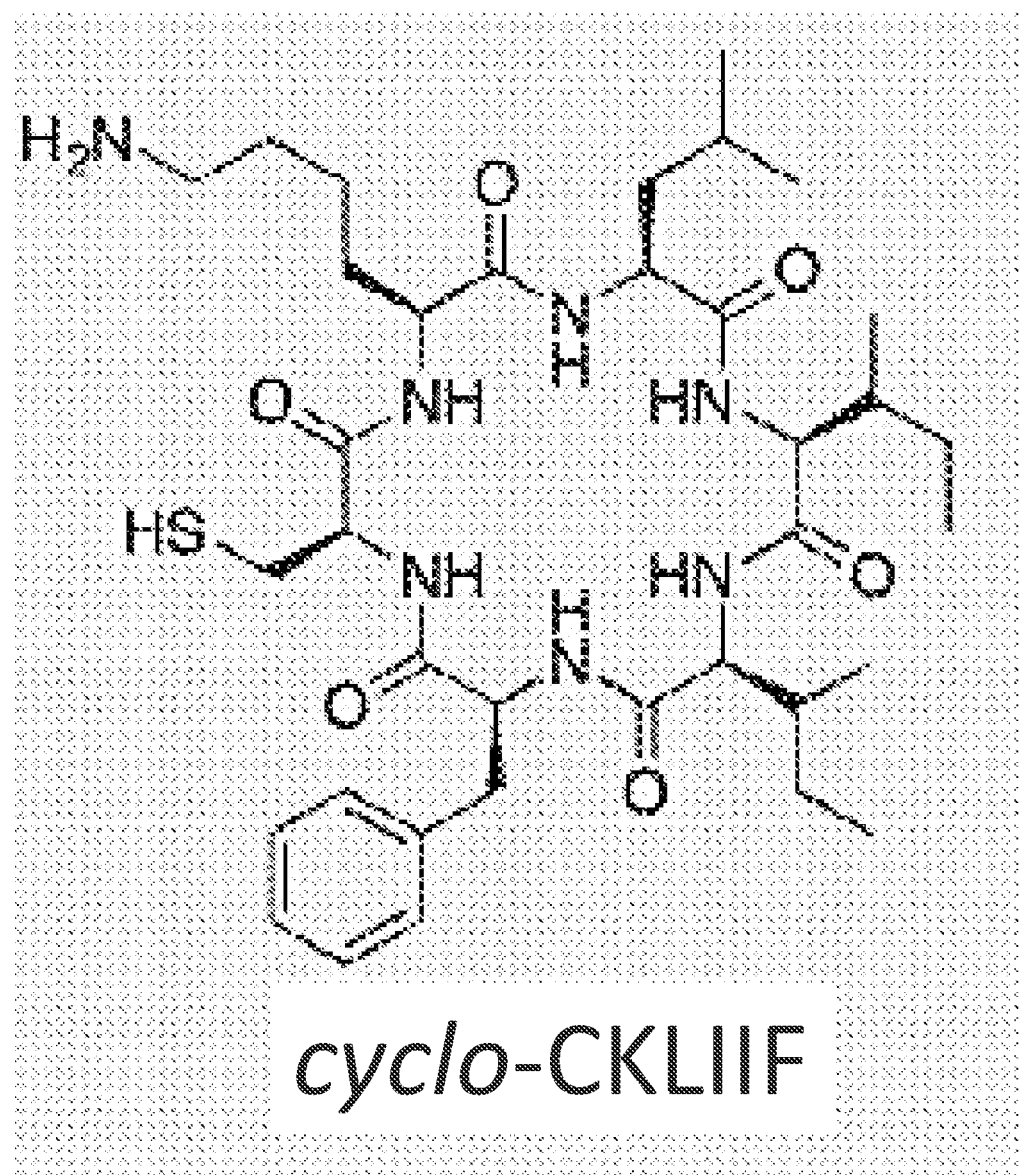
Figure 11A. Structure of the cyclic peptides

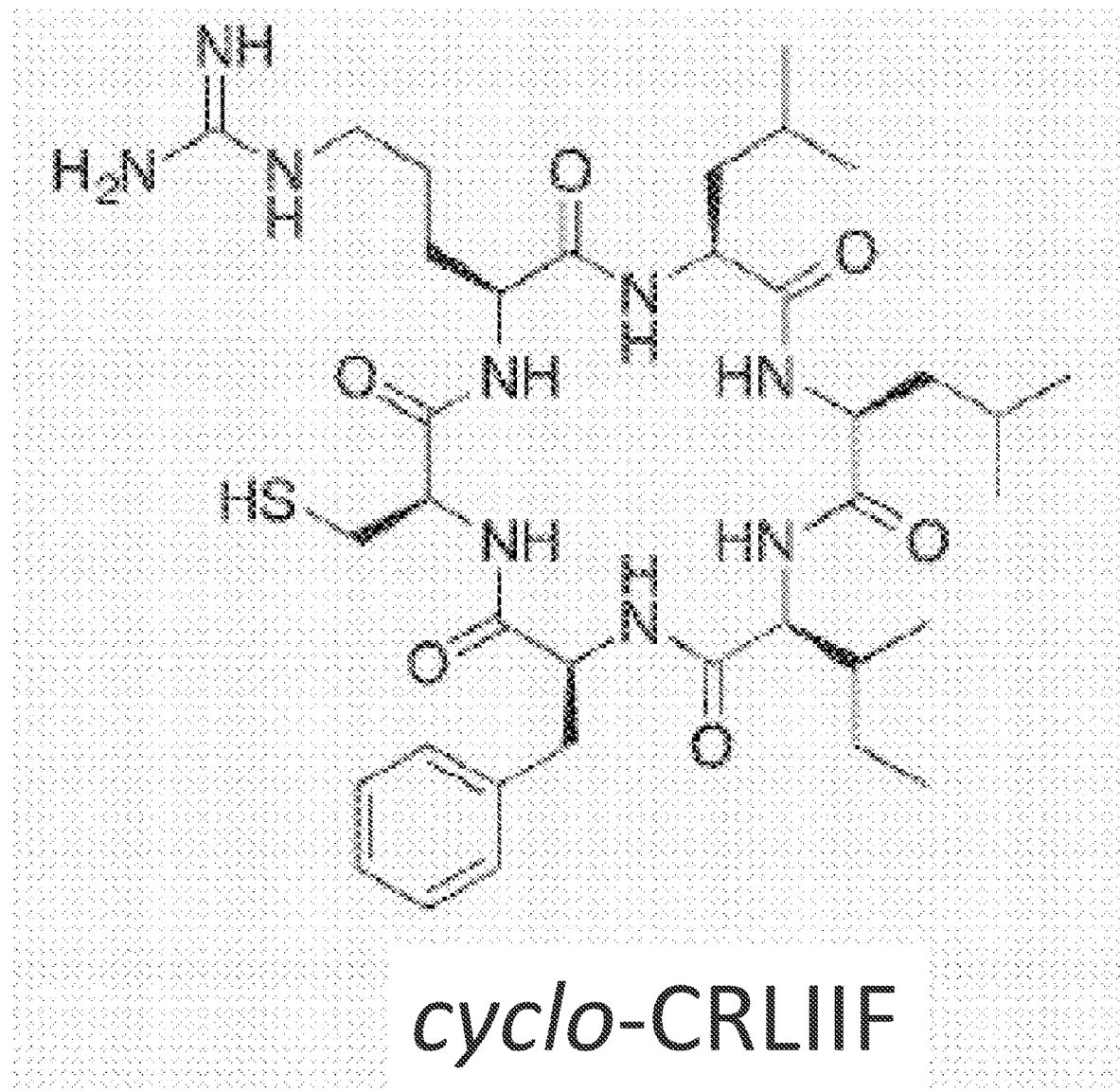
Figure 11B. Structure of the cyclic peptides

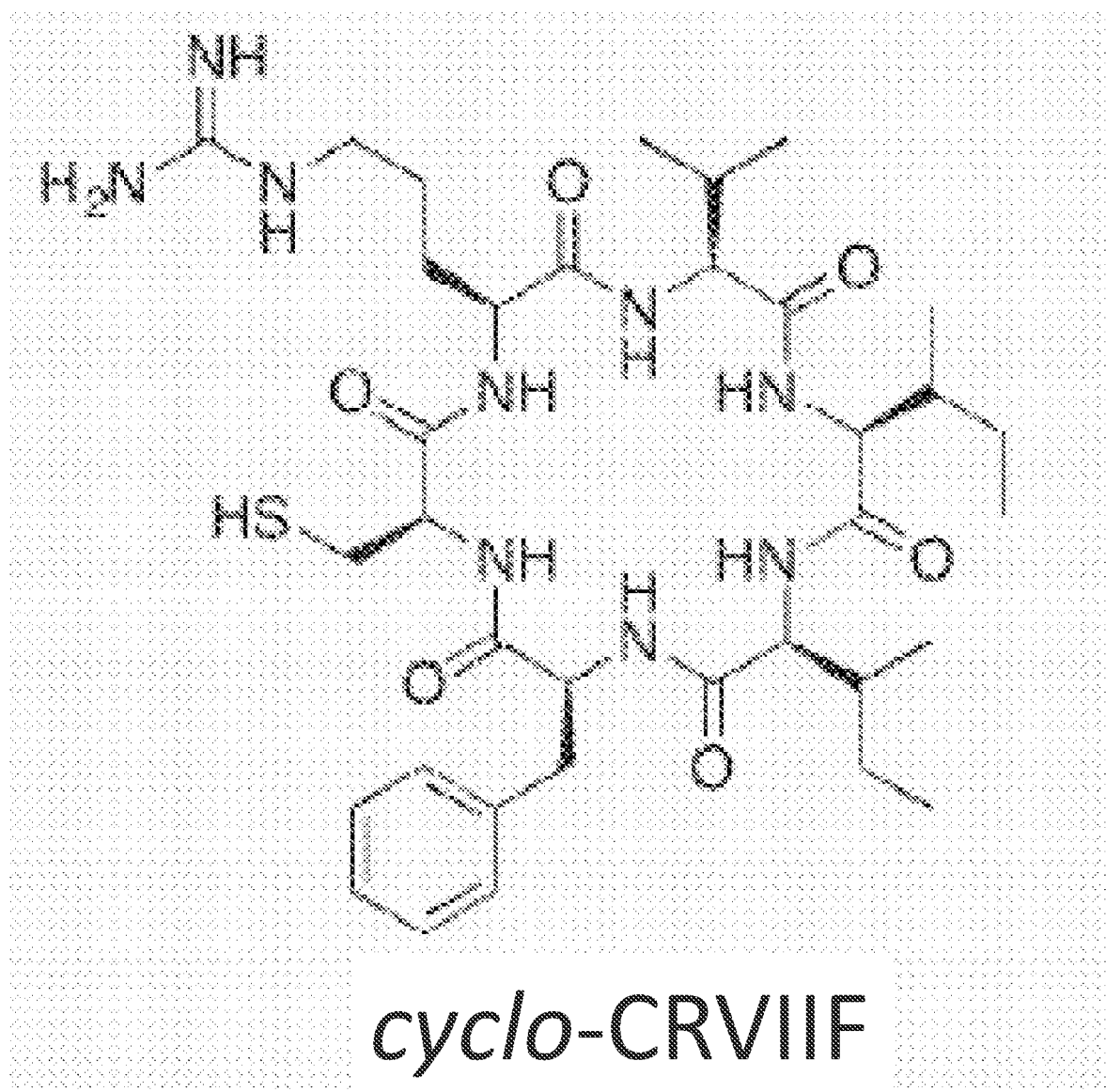
Figure 11C. Structure of the cyclic peptides

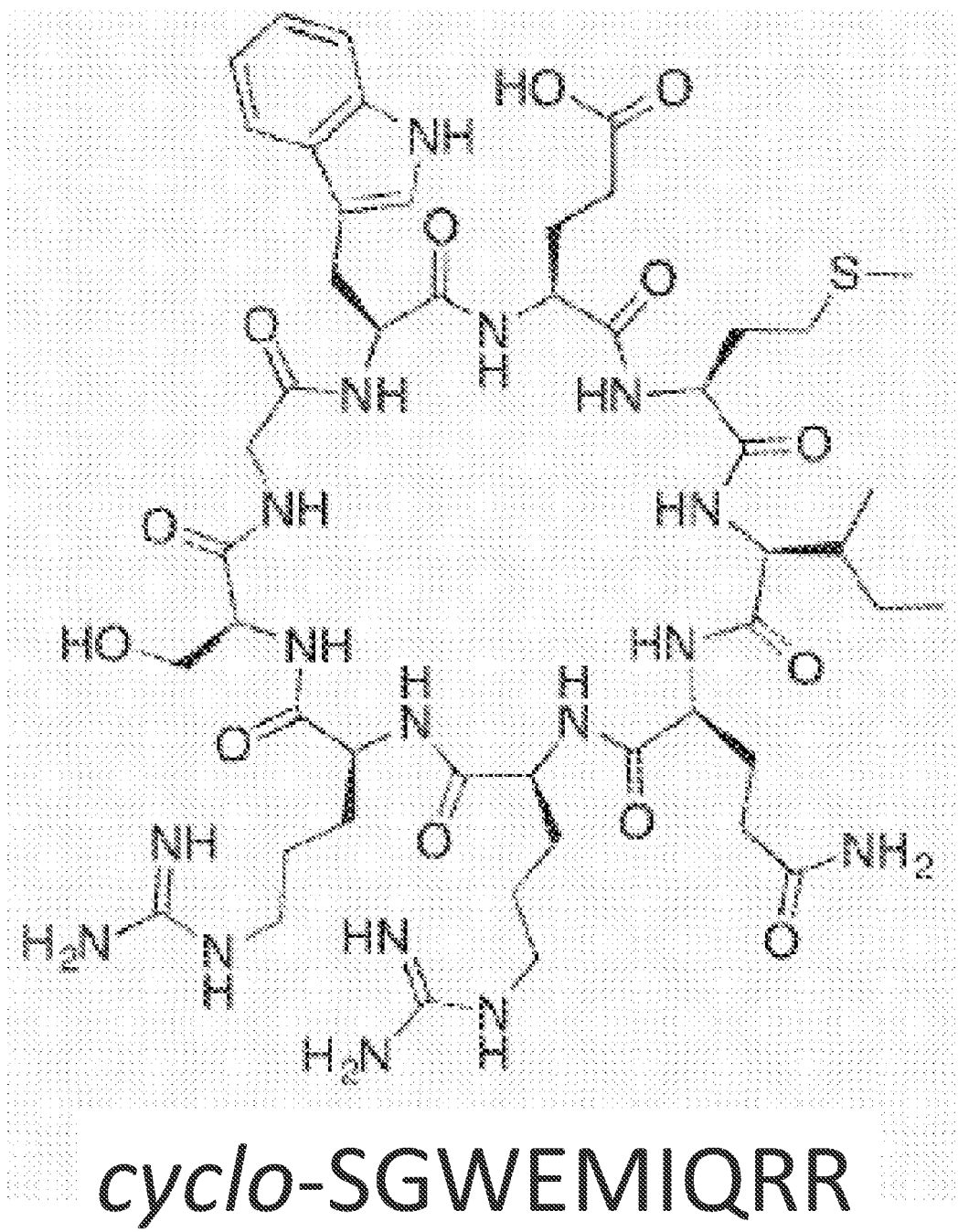
Figure 11D. Structure of the cyclic peptides

HIF-1 AND HIF-2 INHIBITORS

CROSS REFERENCE TO RELATED APPLICATIONS

This application is a U.S. National Phase Application of International Application No. PCT/GB2017/050220, filed Jan. 27, 2017, which claims the benefit of priority of GB Patent Application No. 1601527.3, filed on Jan. 27, 2016, both of which are hereby incorporated by reference in their entirety.

The present invention relates to inhibitors of HIF-1 and HIF-2 and uses thereof. The present invention further relates to the inhibitors for use in treatment of diseases.

Homeostasis of oxygen, a key metabolite, is critical for mammalian cell survival. This necessitates a robust network that senses and rapidly responds to hypoxia (low oxygen levels). The key component of this hypoxia response network is hypoxia inducible factor (HIF), a heterodimeric transcription factor composed of an oxygen-regulated α-subunit and a ubiquitously expressed β-subunit (also known as the aryl nuclear transcription factor or ARNT). Mammals possess three isoforms of HIF-α; the ubiquitously expressed HIF-1α mounts the immediate response to reductions in cellular oxygen, while HIF-2α (also known as EPAS1) and HIF-3α are thought to regulate the response to prolonged hypoxia.

While the intricate interplay between HIF-α isoforms in cancer is complicated and yet to be fully deciphered, the role of HIF-1 activity in angiogenesis, tumour growth, and metastasis is well established. HIF-1α is overexpressed in many cancers, and oncogene activation and loss of tumour suppressor function is shown to be associated with HIF-1 activation. HIF-1α is negatively regulated at the protein level by oxygen via prolyl hydroxylase enzymes that use oxygen as a substrate for the hydroxylation of residues 402 and 564 of HIF-1α, marking it for ubiquitination by an E3 ubiquitin ligase complex and rapid proteolysis. Reduced oxygen levels lead to the stabilization and nuclear translocation of HIF-1α, where it 1β to form the HIF-1 transcription factor complex.

HIF-1 rapidly mounts a transcriptional response to hypoxia by directing the expression of a wide variety of hypoxia response genes. By utilizing changes in the substrate concentration of a continuously occurring enzymatic reaction (hydroxylation of HIF-1α), the cellular response to hypoxia is near instantaneous, with HIF-1α acting as both the sensor and a key component of the hypoxia response machinery. Inhibition of HIF-1 has long been known to hold much potential for cancer therapy; there are multiple possible points for therapeutic intervention in the hypoxia response network, and molecules that inhibit various components of this diverse pathway have been reported, but the absolute requirement for the dimerization of HIF-1α and HIF-1β for DNA binding and transcription activity of the HIF-1 complex makes this protein-protein interaction a seemingly optimal point of interception.

It would be beneficial to have an effective therapeutic inhibitor of HIF-1 and HIF-2. Such inhibitor would be particularly useful in cancer therapy. Accordingly the present invention provides an inhibitor that inhibits the activity of both HIF-1 and HIF2.

In one embodiment the present invention provides an isolated polypeptide that prevents dimerization of HIF-1α with HIF-1β and HIF-2α with HIF-1β and/or inhibits the activity of HIF-1 and HIF-2, wherein the polypeptide comprises the amino acid sequence C-X1-X2-X3-Z-X4 (SEQ ID NO 1) and wherein X1, X2, X3 and X4 are any amino acid and wherein Z is leucine, valine of isoleucine or a non-natural derivative or leucine, valine or isoleucine. A compound, for example an isolated polypeptide, that prevents dimerization of HIF-1α with HIF-1β and HIF-2α with HIF-1β inhibits the activity of HIF-1 and HIF-2. The compound, for example an isolated polypeptide, may bind to HIF-1α or HIF-1β and/or HIF-2α or HIF-1β.

SEQ ID NO: 1=C-X1-X2-X3-Z-X4 relates to a 6 amino acid polypeptide wherein the first amino acid is Cysteine; the second amino acid may be any natural or unnatural amino acid provided that the amino acid chosen results in a polypeptide that is an inhibitor of HIF-1 and/or HIF-2 activity; the third amino acid may be any natural or unnatural amino acid provided that the amino acid chosen results in a polypeptide that is an inhibitor of HIF-1 and/or HIF-2 activity; the fourth amino acid may be any natural or unnatural amino acid provided that the amino acid chosen results in a polypeptide that is an inhibitor of HIF-1 and/or HIF-2 activity, the fifth amino acid may be leucine, valine or isoleucine or a non-natural derivative of leucine, valine or isoleucine and; the sixth amino acid may be any natural or unnatural amino acid provided that the amino acid chosen results in a polypeptide that is an inhibitor of HIF-1 and/or HIF-2 activity.

The isolated polypeptide may be C-X1-X2-X3-I-X4 (SEQ ID NO: 6).

The isolated polypeptide according to claim 1 wherein the peptide comprises the amino acid sequence CXZZZF (SEQ ID NO: 7) wherein: X is arginine or lysine or a non-natural derivative of arginine or lysine; Z is leucine, valine or isoleucine or a non-natural derivative or leucine, valine or isoleucine, optionally aliphatic derivatives can be placed in any of the Z positons in any combination and/or the phenylalanine (F) can be derivative with non-natural analogues and/or optionally a moiety of sulphur is attached in place of C The isolated polypeptide may consist of the sequence CKLIIF (SEQ ID NO: 2).

The polypeptide may be a circular polypeptide. If the peptide is a circular polypeptide the first to fifth positions of the polypeptide may be identified by their relationship to amino acid 1, which is cysteine and 5, which is isoleucine.

The peptide may be cyclic or may be linear. The peptide may be a linear peptide having the sequence C-X1-X2-X3-Z-X4 (SEQ ID NO 1). The peptide may be a cyclic peptide having the sequence C-X1-X2-X3-Z-X4 (SEQ ID NO 1). A cyclic peptide may be cleaved at any position in the ring to provide a linear peptide. The peptide may be a linear peptide having sequence selected from C-X1-X2-X3-Z-X4 (SEQ ID NO 1), X1-X2-X3-Z-X4-C (SEQ ID NO 11), X2-X3-Z-X4-C-X1 (SEQ ID NO 12), X3-Z-X4-C-X1-X2 (SEQ ID NO 13), Z-X4-C-X1-X2-X3 (SEQ ID NO 14) and X4-C-X1-X2-X3-Z (SEQ ID NO 15). The peptide may be derived or derivable by cleaving a cyclic peptide having a sequence C-X1-X2-X3-Z-X4 (SEQ ID NO 1) at the appropriate position to derive the peptide.

The peptide may be a linear peptide having sequence selected from:
CKLIIF (SEQ ID NO 2); KLIIFC (SEQ ID NO 16); LIIFCK (SEQ ID NO 17); IIFCKL (SEQ ID NO 18); IFCKLI (SEQ ID NO 19); FCKLII (SEQ ID NO 20); CRLLIF (SEQ ID NO 3), RLLIFC (SEQ ID NO 21), LLIFCR (SEQ ID NO 22), LIFCRL (SEQ ID NO 23), IFCRLL (SEQ ID NO 24), FCRLLI (SEQ ID NO 25)

CRVIIF (SEQ ID NO 4), RVIIFC (SEQ ID NO 26), VIIFCR (SEQ ID NO 27), IIFCRV (SEQ ID NO 28), IFCRVI (SEQ ID NO 29), FCRVII (SEQ ID NO 30), SGWEMIQRR (SEQ ID NO 5), GWEMIQRRS (SEQ ID NO 31), WEMIQRRSG (SEQ ID NO 32), EMIQRRSGW (SEQ ID NO 33), MIQRRSGWE (SEQ ID NO 34), IQRRSGWEM (SEQ ID NO 35), QRRSGWEMI (SEQ ID NO 36), RRSGWEMIQ (SEQ ID NO 37) and RSGWEMIQR (SEQ ID NO 38).

The peptide may be derived or derivable by cleaving a cyclic peptide having a sequence CKLIIF (SEQ ID NO 2), CRLLIF (SEQ ID NO 3), CRVIIF (SEQ ID NO 4) or SGWEMIQRR (SEQ ID NO 5) at the appropriate position to derive the peptide.

The polypeptide may consist of the sequence CRLLIF (SEQ ID NO: 3).

The polypeptide may consist of the sequence CRVIIF (SEQ ID NO: 4).

The polypeptide may consist of the sequence SGWEMIQRR (SEQ ID NO: 5).

It has been found that circular polypeptides having the sequence set out in SEQ ID NOs: 2, 3, 4 and 5 inhibit the activity of HIF-1 and HIF-2.

The polypeptide may be a derivative of any of the above peptides, for example: where the L amino acids are replaced with D amino acids, and/or the sequences are reversed, and/or one or more of the amides in the backbone is modified (e.g. N-methylated), and/or replaced with isosteres (e.g. a thioester or a fluoroalkene).

Any of the polypeptides described herein may be circular polypeptides. Polypeptides may be circularised by joining the first amino acid to the last amino acid using an amide bond, thioester, or other linkage, for example joining amino acid 1 to amino acid 6 using a thioether or other linkage.

Whether a given polypeptide prevents dimerization of HIF-1α with HIF-1β and HIF-2β with HIF-1β and is an inhibitor of HIF-1 and/or HIF-2 activity may be tested in any suitable way; for example, there are a number of in vitro tests of HIF-1 and HIF-2 activity that may be done in the presence and absence of a candidate inhibitor. Thermal shift data of PASB domains of HIF-1α, HIF-1β and HIF-2α with and without various compounds were used (FIG. 1). Whether a given compound disrupts or prevents dimerization of HIF-1α with HIF-1β and HIF-2α with HIF-1β can be tested using an ELISA test. For example, ELISA showing disruption of HIF-1α/HIF-1β and HIF-2α/HIF-1β dimerization were conducted and the results of these tests are shown in FIG. 2. HIF activity in cells may be tested using cell-based assays that are known in the art.

The binding of the compounds to their targets was assessed by measuring changes in the melting temperature of their target proteins HIF-1α and HIF-2α (known as a thermal shift assay) and by microscale thermophoresis (MST). The data for the thermal shift assay is summarized in FIG. 1, while the binding constants ($K_d$) derived from MST is shown in FIG. 3. Compounds that are effective inhibitors decrease the melting temperatures of the proteins. CKLIIF (SEQ ID NO 2), CRLLIF (SEQ ID NO 3), and CRVIIF (SEQ ID NO 4) show activity against both HIF-1α and HIF-2α in this assay, but not against HIF-1β (negative control). SGWEMIQRR (SEQ ID NO 5) is only active against HIF-1α in this assay. MST data showed mid to low μM $K_d$ values for the polypeptides. The compounds may bind to HIF 1α/2α or 1β in order to disrupt the dimerization, and PASB may be the responsible domain.

The peptides may be modified with non-natural amino acids to give derivatives with improved potency and activity. This is illustrated by the synthesis of derivatives of CRLLIF, where non-natural phenyl alanine derivatives have been used in place of F. The compounds were tested by ELISA and MST, and the data in Table 3 shows a significant (up to 30-fold) improvement in $K_d$ arising from this process (FIG. 5). A similar approach may be taken for the other amino acids in this peptide, and/or the other peptides presented herein.

In another aspect, the present invention provides a polypeptide as described herein for use in medicine.

The polypeptide may be any of the polypeptides described herein or derivatives derived from them that are active in inhibiting the dimerization of HIF-1α with HIF-1β and HIF-2α with HIF-1β and/or the activity of HIF-1 and/or HIF-2. The polypeptide may be formulated in a pharmaceutical composition comprising the polypeptide and physiologically acceptable carrier or excipient.

The polypeptide as described herein or a derivative thereof may be suitable for use in the treatment or prevention of a disease that is treatable or preventable by inhibiting dimerization of HIF-1α with HIF-1β and HIF-2α with HIF-1β and/or the activity of HIF-1 and/or HIF-2.

The polypeptide as describe herein or a derivative thereof may be suitable for use in the treatment or prevention of a disease that is treatable or preventable by preventing dimerization of HIF-1α with HIF-1β and HIF-2α with HIF-1β and/or inhibiting the activity of HIF-1 and HIF-2 inhibiting the activity of HIF-1 and HIF-2.

In another aspect the polypeptides or a derivative thereof described herein may be for use in the treatment or prevention of cancer. Pathways involving HIF-1 and HIF-2 are particularly important in the growth and development of a variety of cancers because cancerous cells are often in a hypoxic environment. HIF-1 inhibitors are proposed to be of potential significance as therapeutics for a large variety of cancers, whereas HIF-2 inhibition is proposed to be of potential significance in renal cell carcinoma and digestive system cancers.

The polypeptides described herein or a derivative thereof may be used in the treatment of any type of cancer, for example a cancer selected from list 1.

List 1

Acute lymphoblastic leukemia (ALL), Acute myeloid leukemia, Adrenocortical carcinoma, AIDS-related cancers, AIDS-related lymphoma, Anal cancer, Appendix cancer, Astrocytoma, childhood cerebellar or cerebral, Basal-cell carcinoma, Bile duct cancer, extrahepatic (see cholangiocarcinoma), Bladder cancer Bone tumor, osteosarcoma/malignant fibrous histiocytoma, Brainstem glioma Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Breast cancer, Bronchial adenomas/carcinoids, Burkitt's lymphoma, Carcinoid tumor, childhood, Carcinoid tumor, gastrointestinal, Carcinoma of unknown primary, Cerebellar astrocytoma, Cerebral astrocytoma/malignant glioma, Cervical cancer, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, Ependymoma, Esophageal cancer, Ewing's sarcoma, Extracranial germ cell tumor, Extragonadal germ cell tumor, Extrahepatic bile duct cancer, intraocular melanoma, retinoblastoma, Gallbladder cancer, Gastric (stomach) cancer, Gastrointestinal carcinoid tumor, Gastrointestinal stromal tumor (GIST), Germ cell tumor: extracranial, extragonadal, or ovarian, Gestational trophoblastic tumor, Glioma of the brain stem, Glioma, childhood cerebral astrocytoma, Glioma, childhood visual pathway and hypothalamic, Gastric carcinoid, Hairy cell leukemia, Hepatocellular (liver) cancer, Hodgkin lymphoma, Hypopharyngeal cancer, Hypothalamic and visual pathway glioma, childhood, Intraocular melanoma, Islet cell carcinoma (endocrine pancreas), Kaposi sarcoma, Kidney cancer (renal cell cancer), Laryngeal cancer, Leukaemias, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphomas, Lymphoma, AIDS-related, Lymphoma, Burkitt, Lymphoma, cutaneous T-Cell, Lymphoma, Hodgkin, Lymphomas, Non-Hodgkin, Lymphoma, primary central nervous system, Macroglobulinemia, Waldenström, Malignant fibrous histiocytoma of bone/osteosarcoma, Medulloblastoma, Melanoma, Merkel cell cancer, Mesothelioma, Mouth cancer, Multiple endocrine neoplasia syndrome, Multiple myeloma/plasma cell neoplasm, Mycosis fungoides, Myelodysplastic syndromes Myelodysplastic/myeloproliferative diseases, Myelogenous leukemia, chronic Myeloid leukemia, adult acute, Myeloid leukemia, childhood acute, Myeloma, multiple (cancer of the bone-marrow), Myeloproliferative disorders, chronic, Myxoma, Nasal cavity and paranasal sinus cancer, Nasopharyngeal carcinoma Neuroblastoma, Non-Hodgkin lymphoma, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, childhood, Pituitary adenoma Plasma cell neoplasia/Multiple myeloma, Pleuropulmonary blastoma, Primary central nervous system lymphoma, Prostate cancer, Rectal cancer, Renal cell carcinoma, Renal pelvis and ureter, transitional cell cancer, Rhabdomyosarcoma, childhood, Salivary gland cancer, Sarcoma, Ewing family of tumors, Sarcoma, Kaposi, Sarcoma, soft tissue, Sarcoma, uterine, Sézary syndrome, Skin cancer (non-melanoma), Skin cancer (melanoma), Skin carcinoma, Merkel cell, Small cell lung cancer, Small intestine cancer, Soft tissue sarcoma, Squamous cell carcinoma—see skin cancer (non-melanoma), Squamous neck cancer with occult primary, metastatic, Stomach cancer, Supratentorial primitive neuroectodermal tumor, childhood, T-Cell lymphoma, cutaneous, Testicular cancer, Throat cancer, Thymoma, Thymoma and thymic carcinoma, Thyroid cancer, Thyroid cancer, Transitional cell cancer of the renal pelvis and ureter, Trophoblastic tumor, gestational, Unknown primary site, Ureter and renal pelvis, transitional cell cancer, Urethral cancer, Uterine cancer, endometrial, Uterine sarcoma, Vaginal cancer, Visual pathway and hypothalamic glioma, Vulvar cancer, Waldenström macroglobulinemia and/or Wilms tumor (kidney cancer).

The polypeptide may be formulated for simultaneous or subsequent administration with another drug or chemotherapeutic agent. This agent may be any known drug or chemotherapeutic agent.

The polypeptide may be for use in the treatment or prevention of Von Hippel-Lindau disease, or any other disease where HIF-1, HIF-2 or hypoxia response is identified as a potential mechanism for therapeutic targeting.

In another aspect the present invention provides, a method of treating or preventing cancer comprising the step of administering an effective amount of a polypeptide according to the present invention to a subject in need thereof.

The polypeptide may be administered by any route, for example orally, by injection, intravenously, or topically.

In a further aspect the polypeptides described herein or its derivative(s) may be used to inhibit dimerization of HIF-1 and/or HIF-2 in vitro. This is particularly useful in experiments to investigate the pathways comprising HIF-1 and HIF-2.

In a further aspect the polypeptides described herein may be used in a method of designing or identifying another HIF-1 and/or HIF-2 inhibitor in drug discovery.

The polypeptides may be used in a method for designing or identifying a drug that also disrupts the HIF-1α/HIF-1β and/or HIF-2α/HIF-1β interaction, for use in the treatment of cancer or other diseases that would benefit from HIF-targeted therapy.

The peptides may be used in a method for designing a small-molecule inhibitor of HIF-1 and/or HIF-2, comprising the step of designing a small molecule mimic of one of the polypeptides or a part thereof. This may be any method known in the art. Once a polypeptide inhibitor is known then small molecules that mimic the shape, orientation and other properties such as charge or hydrophobicity may be created, for example using high-throughput screening, or computer-aided techniques. The small molecules may be tested to ensure that they have a similar activity in inhibiting HIF-1 and/or HIF-2 activity and/or dimerization.

A small-molecule inhibitor of HIF-1 and/or HIF-2 may be designed to mimic the size, shape and/or orientation of amino acids 1, 4 and 5 of SEQ ID NO: 2 since these amino acids are found to be most important for the function of inhibiting HIF-1 and HIF-2 activity.

A small-molecule inhibitor of HIF-1 and/or HIF-2 may be designed to mimic the size, shape and/or orientation of 2, 3, 4, 5 or all 6 amino acids of SEQ ID NO: 2, 3 or 4.

A small molecule inhibitor of HIF-1 and/or HIF-2 may be identified by high-throughput screening, using variants of the compounds disclosed herein, tagged with a fluorescent probe (e.g. fluorescein), to act as a reporter of molecules from a library binding to, and displacing the molecules reported here. A variety of assays may be used for this purpose, e.g. fluorescent polarization, an example is reported in FIG. 4.

In a further aspect the present invention provides a small-molecule that inhibits the dimerization and/or activity of HIF-1 and/or HIF-2 and is identified or designed using one of the method of the present invention.

In a further aspect the present invention provides a small molecule inhibitor of the activity of HIF-1 and/or HIF-2 for use in the treatment of cancer or any disease treatable or preventable by inhibiting or preventing dimerization of HIF-1α with HIF-1β and HIF-2α with HIF-1β and/or inhibiting the activity of HIF-1 and HIF-2.

The skilled person will understand that optional features of one embodiment or aspect of the invention may be applicable, where appropriate, to other embodiments or aspects of the invention.

In a further aspect, the polypeptides may be modified to improve their pharmacokinetic and pharmacodynamic properties for direct use as therapeutics. Modified peptides may be called derivatives.

Derivatives of the peptides of the invention include:
Peptides of the invention where one or more L amino acids is replaced with D amino acids;
Peptides of the invention where the LLI motif is replaced with any combination of natural or non-natural aliphatic amino acids, for example valine, leucine, homoleucine or isoleucine;
Peptides of the present invention wherein their side chains are substituted with any atom or functional group, for example H or an alkyl group;
A peptide of the present invention wherein one or more side chain is substituted with phenyl, para-chlorophenyl, cyclohexyl, naphthyl, pyridyl or other aromatic rings;
The peptide may be any of the derivatives shown in FIG. 4,
A peptide selected from: CRLLI(4-Me-F), CKLII(4-Me-F), CRVII(4-Me-F), CRLL(Nal), CKLII(Nal), CRVII(Nal), CRLLI(Cha), CKLII(Cha), CRVII(Cha), CRLLI(4-Cl-F), CKLII(4-Cl-F), CRVII(4-Cl-F), CRLLIW, CKLIIW, and CRVIIW,
wherein the derivative is active in inhibiting the dimerization of HIF-1α with HIF-1β and HIF-2α with HIF-1β and/or the activity of HIF-1 and/or HIF-2.

Examples of potential sites for modification for cyclo CRLLIF (SEQ ID NO 3) are shown in FIG. 4.

There now follows by way of example only a detailed description of the present invention with reference to the accompanying drawings, in which;

BRIEF DESCRIPTION OF THE DRAWINGS

FIG. 1 shows the thermal shift results for cyclic peptide inhibitors disrupting HIF-1α/HIF-1β and HIF-2α/HIF-1β interactions.

A) inhibitors were assayed for ability to disrupt the HIF-1α/HIF1-β protein-protein interaction. B) inhibitors were assayed for the ability to disrupt the HIF-2α/HIF1-β protein-protein interaction.

FIGS. 2A and 2B show ELISA results for cyclic peptide inhibitors disrupting HIF-1α/HIF-1β and HIF-2α/HIF-1β interactions.

FIGS. 3A-3C show MST results for cyclic peptide inhibitors binding to HIF-1α and HIF-2α, and CRVIIF (SEQ ID NO 4) affecting the dimerization constant of HIF-2α/HIF-1β. A) HIF-1α, B) HIF-2α, C) the $K_d$ of the HIF-1α/HIF1-β protein-protein interaction increases in the presence of 50 µM CRVIIF.

FIGS. 4A-4C exemplify one strategy for improving the potency of the identified molecules. A) Structure of cyclo-CRLLIF (SEQ ID NO 3). B) Potential sites for generation of analogues. X=atom, e.g. S or O; R and $R^1$=any atom or functional group, e.g. H, Me, Et; $R^2$=replacement of the LLI motif with any combination of aliphatic amino acids (natural or non-natural) e.g. valine, leucine, homoleucine, isoleucine. $R^3$=any substituted phenyl, cyclohexyl, naphthyl, pyridyl, or other ring. Amino acids may be L or D in any or all positions, as well as the reverse sequence. The arginine may be replaced with lysine, ornithine or other nitrogen containing non-natural amino acids. C) The derivatives generated in this study.

FIGS. 5A-5B show MST results for the most potent derivatives of CRLLIF (SEQ ID NO 3) binding to HIF-1α and HIF-2α. A) Binding affinity of given derivative for the PAS-B domain of HIF-1α. B) Binding affinity of given derivative for the PAS-B domain of HIF-2α.

FIG. 6 shows a fluorescently tagged derivative of CRVIIF (SEQ ID NO 4) binding to the PAS B domain of HIF-2α by ELISA (upper panel) and fluorescence polarization (lower panel).

FIGS. 7A-7B. A) Residues on the PAS B domain of HIF-2α that are affected by CRVIIF (SEQ ID NO: 4), as identified by $N^{15}$ NMR. B) A ribbon diagram of 2a PASB with CRVIIF (SEQ ID NO: 4).

FIG. 8 shows ribbon (left panel) and surface models (middle and right panel) showing the proposed binding site of CRVIIF (SEQ ID NO 4), FIGS. 9A and 9B show the results of alanine scanning of CRVIIF (SEQ ID NO 4), assessed by ELISA. A) assessed by HIF-1α/HIF1-β ELISA. B) assessed by HIF-2α/HIF1-β ELISA.

FIG. 10 shows the results of cell permeability and localisation of fluor-CRVIIF (SEQ ID NO 4). Compound (top right of each panel) appears to cross cell membrane, and either localises inside vesicles (bottom left of each panel), in the cytoplasm, or crosses into the nucleus (bottom right of each panel).

FIGS. 11A-11D show the structures of cyclic versions of SEQ ID NO: 5 (A); SEQ ID NO: 3 (B); SEQ ID NO: 4 (C); and SEQ ID NO: 2 (D).

EXPERIMENTAL RESULTS 4 cyclic peptide hits were identified using a SICLOPPS screen to identify cyclic peptide inhibitors of HIF1 and HIF2.

Thermal shift data of thioredoxin-tagged longer constructs and PASB domains with the identified polypeptides are shown in FIG. 1. Compounds that are effective inhibitors decrease the melting temperatures of the proteins. Compound C (CRVIIF) (SEQ ID NO 4) is most potent as can be seen from the downwards shift in the melting curve.

ELISA with thioredoxin-tagged HIF-1α/2α and GST-tagged HIF-1β (bHLH-PASA-PASB domain constructs) was used to determine whether compounds inhibit dimerisation of HIF heterodimer in vitro. Data is shown in FIG. 2. CKLIIF (SEQ ID NO 2) was found to be the most potent, of the 4 identified cyclic peptides in this assay, for inhibiting the binding of HIF-1β to 1α/2α. $IC_{50}$ values for the compound=3.7 µM/8.8 µM for 1α/2α.

TABLE 1 showing the melting temperatures with each of compounds A-D

| | $\Delta T_m$ (° C.) | | | | | |
|---|---|---|---|---|---|---|
| Compound | Trx-1α | Trx-2α | GST-1β | 1α PASB | 2α PASB | 1β PASB |
| 1 mM CRLLIF (SEQ ID NO 3) | 0.5 | −4 | | −2 | −4 | −1 |
| 1 mM CKLIIF (SEQ ID NO 2) | −1.5 | −2.5 | | −1 | −2.5 | −0.5 |
| 1 mM CRVIIF (SEQ ID NO 4) | −1 | −2 | −0.5 | −1.5 | −2.5 | −0.5 |
| 1 mM SGWEMIQRR (SEQ ID NO 5) | −2.5 | −2 | | −0.5 | −2.5 | −0.5 |

ELISA assays were conducted using 1α/2α PASB domains. The results, shown in FIG. 2, shows comparable $IC_{50}$ values to longer Trx-tagged constructs (5.4 µM vs. 3.7

µM for 1α, 15.2 µM vs. 8.8 µM for 2α). The results in FIG. 2 suggest PASB domain dimerisation is the main target of inhibition by CRVIIF (SEQ ID NO 4).

Microscale thermophoresis (MST) was performed to determine $K_d$ of peptide binding to fluorescently labelled HIF-1α/2α PASB domains. The results are shown in FIG. 3.

MST competition assay was used to measure inhibition of heterodimerisation: 1β PASB domain titrated into 2α PASB domain. The binding affinity of these two proteins was determined in absence and presence of 50 µM CRVIIF (SEQ ID NO 4): $K_d$=378 nm in absence of CRVIIF (SEQ ID NO 4), 3.7 µM in presence of CRVIIF (SEQ ID NO 4). The data shows that CRVIIF (SEQ ID NO 4) shifts the binding equilibrium between HIF-2α and 1β PASB domains as seen in FIG. 3, right hand panel.

Improving the affinity of the identified cyclic peptides using non-natural amino acids: FIG. 4 exemplifies one strategy that may be used to improve potency of the identified molecules.

FIG. 5 shows the potency of the identified molecules may be significantly improved by substituting one of the amino acids (F) for a natural (W) or non-natural equivalent (e.g. naphthyl). Full list of molecules synthesized, and characterization data by ELISA and MST are shown in table 3.

Validation of fluor-CRVIIF (SEQ ID NO 4): point ELISA shows similar inhibition of dimerisation compared to unlabelled CRVIIF as shown in FIG. 6.

The fluorescent tag appears not to interfere with binding or inhibition of dimerisation. Fluorescence polarisation (FP) assay: titration of 2α PASB into 2 µM fluor-CRVIIF (SEQ ID NO 4) gives $K_d$ of 18.5 µM.

FIG. 7 shows NMR using 15N labelled 2α PASB+/−CRVIIF (SEQ ID NO 4). Slight shifts can be seen from the 15N labelled backbone amides in presence of CRVIIF (SEQ ID NO 4). Backbone amide peaks were assigned to residues using double labelled 13C 15N 2α PASB. Backbone amide peaks that shifted in presence of CRVIIF (SEQ ID NO 4) correspond mainly to residues surrounding the internal water cavity. This suggests CRVIIF (SEQ ID NO 4) induces a conformational change that affects binding of water molecules inside the cavity.

In the absence of detailed NMR data, a potential binding site of CRVIIF (SEQ ID NO 4) was proposed based on the published crystal structures of 2α-1β PASB domains. CRVIIF (SEQ ID NO 4) appears to mimic a region of 1β at the α-β binding interface. 2 isoleucine residues and a phenylalanine point into hydrophobic pockets on the surface of 1α/2α, an arginine residue forms a water-mediated bond to Arg258/260 of 1α/2α, and Leu243/245 of 1α/2α forms hydrophobic protrusion towards the central ring of the CRVIIF (SEQ ID NO 4) motif.

This suggests CRVIIF (SEQ ID NO 4) may act in direct competition with 1β. 1α and 2α are almost identical at the proposed binding site (FIG. 8). The only difference is Val336 in 1α is a methionine in 2α, which may explain slightly better $IC_{50}$ and $K_d$ values obtained for 1α vs. 2α.

ELISA using alanine scan peptides with 1α/2α PASB domains and GST-1β identified residues 1, 4, 5 of CRVIIF (SEQ ID NO 4) as critical for inhibiting dimerization (FIG. 9), i.e. inhibitory activity is reduced when these are mutated to alanine. Residues 2, 3 and 6 also important but to a lesser extent. Residues 4 and 5 (both isoleucines) fit well with the proposed binding site model, where 2 Ile residues point into hydrophobic pockets on the surface of 1α/2α.

Site-directed mutagenesis was used to make mutations in 1α/2α PASB domains at the proposed binding site, and corresponding domain-swapped mutations in 1β to still allow heterodimerisation. Mutations should inhibit binding of CRVIIF (SEQ ID NO 4) to 1α/2α if the proposed binding site is correct.

FIG. 10 shows cell permeability tested using fluorescently labeled-CRVIIF (SEQ ID NO: 4) in MCF-7 cells. Compound (top right of each panel) appears to cross cell membrane, and either localises inside vesicles (bottom left of each panel), in the cytoplasm, or crosses into the nucleus (bottom right of each panel).

FIG. 11 shows the structure of the identified cyclic peptides

Materials and Methods
Reagents from Fisher/Sigma unless specified otherwise
Constructs for Protein Expression
The expression constructs used to produce proteins for this work are listed in Table 2.

TABLE 2

Constructs for protein expression

| Protein ID | Domain | Vector | Cloning sites | Construct |
|---|---|---|---|---|
| 1α PASB | 238-349 | pET28 | BamH1/Sac1 | $His_6$-Met[Protein] |
| 2α PASB | 240-350 | pET28 | BamH1/Sac1 | $His_6$-Met[Protein] |
| 1β PASB | 356-474 | pET28 | Nde1/Sac1 | $His_6$-[Protein] |
| Trx-1α | 1-350 | pET32 | BamH1/Eag1 | Thioredoxin-$His_6$-[Protein] |
| Trx-2α | 1-360 | pET32 | BamH1/Xho1 | Thioredoxin-$His_6$-[Protein] |
| GST-1β | 1-474* | pGEX-2TK | BamH1/EcoR1 | GST-[Protein] |
| 2α $PASB^{R260A}$ | 240-350 | pET28 | BamH1/Sac1 | $His_6$-Met[Protein] |

*Isoform 2, Δ77-91

Site-Directed Mutagenesis

Site-directed mutagenesis was performed following a QuikChange protocol (Agilent) using either 2× Phusion HF Master Mix (NEB) or Pfu polymerase (Promega) following the manufacturers' recommended conditions for thermal cycling. PCR products were treated with 1 µL Dpn1 (NEB) for 1 hr at 37° C., then 5 µL of each reaction were used to transform 50 µL chemically competent DH5α via heat shock (42° C., 45 sec). Recovered cells were plated on LB agar plates supplemented with 50 µg/mL kanamycin. Individual colonies were picked and sequenced (Eurofins) to confirm the desired mutation.

Protein Expression

The proteins used in this study were produced and purified per previously published protocols (e.g. Miranda E. et al., J. Am. Chem. Soc., 2013, 135 (28), 10418-10425; and Scheuermann T. H. et al., Nat. Chem. Bio., 2013, 9 (4), 271-276).

Thermal Shift Assay

Thermal denaturation of HIF proteins was performed in 20 µL reactions in triplicate using a Bio-Rad CFX Connect Real-Time System. Proteins were used at either 5 µM (Trx-1α, Trx-2α and GST-1β) or 15 µM (His-tagged PASB domains) in HIF assay buffer, with 10 mM DTT and SYPRO orange dye (Life Technologies) at a final concentration of 8× (relative to 5000× stock), and supplemented with either DMSO or compound dissolved in DMSO at the stated concentrations. The reaction plate was assembled on ice, then transferred to the pre-chilled thermal cycler, held at 10° C. for 5 min (heated lid, 105° C.), then the temperature ramped to 95° C. Fluorescence was recorded at 0.5° C. increments, holding for 5 sec at each temperature. Data were plotted using GraphPad Prism 6, and melting temperatures calculated using the first derivative method in which the peak (i.e. the steepest transition between data points) represents the point at which 50% of the protein sample is denatured. Errors are quoted as the inherent error associated with the first derivative of the data, i.e. ±0.25° C. for $T_m$ values and ±0.5° C. for $\Delta T_m$ values.

ELISA

25 µL of His-tagged HIF-α protein (either Trx-1α, Trx-2α, 1α PASB, or 2α PASB) at 0.1 µM in HIF assay buffer were added to individual wells of a Pierce $Ni^{2+}$-coated 96-well plate (Thermo) in triplicate. The plate was rocked gently at room temperature for 1 hr, before washing with 3×200 µL assay buffer (5 min incubation per wash). 25 µL of compounds and/or DMSO at the stated concentrations were added to the plate and allowed to equilibrate for 30 min prior to the addition of 25 µL of GST-1β at 0.2 µM in assay buffer for 1 hr. For conditions in which no compound or DMSO were used, GST-1β was added as a 0.1 µM solution. After incubation with GST-1β, the wells were washed with 3×200 µL assay buffer then 1×200 µL PBS. The wells were then incubated with 100 µL mouse α-GST antibody (Thermo, MS-707-P) at a 1/1000 dilution in PBS supplemented with 0.1% Tween-20 (PBST) and 2% non-fat powdered milk (Marvel) for 1 hr, followed by 3×200 µL washed with PBS. 100 µL of secondary HRP-conjugated α-mouse antibody (GE Healthcare) was added at a 1/6000 dilution in 2% milk/PBST for 1 hr, then washed with 3×200 µL PBS. Wells were incubated with 100 µL of 1-Step Ultra TMB-ELISA solution (Thermo) until a blue colour developed (typically 10-15 min) and the reaction was stopped by the addition of 100 µL of a ⅕ dilution of conc. $H_2SO_4$, which turned the solution yellow. Absorbance was read at 450 nm using a Tecan Infinite M200 Pro plate reader. Data were fitted and $IC_{50}$ values determined by non-linear regression using GraphPad Prism 6.

Microscale Thermophoresis 0.5 mL of 1α or 2α PASB protein stocks in HIF storage/assay buffer were dialysed against 1 L of MST labelling buffer (100 mM $NaHCO_3$ pH 8, 150 mM NaCl and 5% glycerol) for 1.5 hr at 4° C., then against 1 L of fresh labelling buffer at 4° C. overnight. 100 µL of each dialysed protein diluted to 10 µM were incubated with 100 µL of 30 µM NT-647-NHS dye (NanoTemper protein labelling kit) for 20 min in the dark, then exchanged into 650 µL HIF assay buffer supplemented with 0.05% Tween-20 using the supplied gravity flow purification columns. A dilution series of cyclo-CRVIIF (SEQ ID NO 4) or alanine scan analogues (in HIF assay buffer, 10% DMSO) was mixed with equal volumes of labelled 1α PASB or 2α PASB at 100 nM and allowed to equilibrate for 10 min. Samples were loaded into hydrophilic capillaries and, after optimising the power, MST was performed using a Monolith NT.155 instrument (NanoTemper). Data were analysed using NT Analysis Software using the Temperature Jump analysis mode.

For competition assays, NT-Red-labelled 2α PASB (100 nM) was mixed with equal volumes of a dilution series of unlabelled 1β PASB (67 µM stock), then each 9 µL sample was supplemented with 1 µL 500 µM cyclo-CRVIIF (SEQ ID NO 4) (50% DMSO) to give final concentrations of 45 nM 2α PASB, 50 µM cyclo-CRVIIF (SEQ ID NO 4), 5% DMSO, and variable 1β PASB (30 µM highest concentration). MST was performed and data analysed as described above.

Fluorescence Polarisation $K_d$ values were determined by fluorescence polarisation (FP) using fluorescently labelled cyclo-CRVIIF (fluor-CRVIIF) (SEQ ID NO 4) dissolved in DMSO as the probe. In each condition, the concentration of the probe was kept constant (2 µM, 1% DMSO) whilst proteins were titrated. Reactions were performed in HIF assay buffer with the addition of 0.1% Triton X-100. Samples were assembled in black 96-well plates (40 µL/well, in triplicate) and allowed to equilibrate for 2 hr in the dark. Plates were read using a POLARstar Omega plate reader (BMG Labtech) at Ex: 490 nm, Em: 520 nm, with target gain set to 300 mP. Polarisation data were plotted and $K_d$ values calculated by non-linear regression using GraphPad Prism 6.

Competition Assay

A competition assay may be employed for the identification of other molecules that competitively bind to HIF-1α or HIF-2α by measuring displacement of the fluor-CRVIIF (SEQ ID NO 4) from the protein.

Cell Culture

For initial compound permeability experiments, 1.5 mL MCF-7 cells were plated on 3 cm petri dishes (200,000 cells/plate) and grown at 37° C. After 24 hr, cells were incubated with fresh media containing the stated concentrations of fluor-CRVIIF (SEQ ID NO 4) (0.5% DMSO) or 66 µM CP-61 control compound (0.66% DMSO) for a further 24 hr. Cells were washed twice with PBS and imaged live in plates. For co-localisation experiments, an 8-well Lab-Tek Chamber Slide (Nunc) was treated with collagen prior to plating 25,000 MCF-7 cells/well. After 24 hr, cells were dosed with 300 µL fresh media containing the stated concentrations of fluor-CRVIIF (SEQ ID NO 4) (0.5% DMSO) and/or 5 µg/mL FM 4-64FX Membrane Stain (Life Technologies) and incubated for a further 24 hr. Cells were washed with 2×300 µL PBS, fixed with 150 µL 10% formalin in PBS for 5-10 min, then washed again with PBS. Growth chambers were removed and nuclear staining was achieved using Vectashield Mounting Medium with DAPI (Vector Laboratories) prior to sealing the slide with a coverslip. Cells were imaged using a fluorescent microscope.

Peptide Synthesis

Cyclic peptides were synthesized by solid phase peptide synthesis, as detailed in Miranda et al. J. Am. Chem. Soc., 2013, 10418.

Derivatives

Derivatives of the above compounds may also be used in the present invention. These are as detailed below with cyclo-CRLLIF (SEQ ID NO 4) as an example but similar derivatives may be made of any of the compounds described herein provided that the derivatives inhibit the activity of HIF-1 and HIF-2.

The derivatives may be derivatives of:
C-X1-X2-X3-Z-X4 (SEQ ID NO 1) wherein X1, X2, X3 and X4 are any amino acid;
CRVIIF (SEQ ID NO: 2);
CRLLIF (SEQ ID NO: 3);
CKLIIF (SEQ ID NO: 4); or SGWEMIQRR (SEQ ID NO: 5), wherein the L amino acids are replaced with D amino acids and the sequences are reversed.

The derivatives may comprise the same motif of CXZZZF (SEQ ID NO 7) where X=arginine or lysine (and so can be replaced with any natural or non-natural derivative of these two amino acids), Z=leucine, valine, or isoleucine and these amino acids or non-natural derivatives, as well as aliphatic derivatives can be placed in any of these 3 positions in any combination. There may also be derivatisation at the phenylalanine with non-natural analogues and/or attachment of a moiety to the sulphur. The cysteine may also be replaced with natural or non-natural amino acids.

Data showing activity of the above molecules (FIG. 10C) in HIF-1 and HIF-2 ELISA (showing the compounds disrupt dimerization of these protein-protein interactions) as well as the binding constants determined by microscale thermophoresis (MST) for binding to the PASB domain of HIF-1α and HIF-2α.

TABLE 3

HIF-1 and HIF-2 inhibitory activity of CRLLIF (SEQ ID NO 3) and its analogues shown in FIG. 4

| CRLLIX where X = | $IC_{50}$ (μM) in HIF-1 ELISA | $IC_{50}$ (μM) in HIF-2 ELISA | $K_d$ (μM) for HIF-1α by MST | $K_d$ (μM) for HIF-2α by MST |
|---|---|---|---|---|
| F | 71.32 | 98.27 | 36.93 | 15.43 |
| 4-Me-F | 11.9 | 6.07 | 9.61 | 5.27 |

TABLE 3-continued

HIF-1 and HIF-2 inhibitory activity of CRLLIF (SEQ ID NO 3) and its analogues shown in FIG. 4

| CRLLIX where X = | $IC_{50}$ (μM) in HIF-1 ELISA | $IC_{50}$ (μM) in HIF-2 ELISA | $K_d$ (μM) for HIF-1α by MST | $K_d$ (μM) for HIF-2α by MST |
|---|---|---|---|---|
| 4-F-F | 37.46 | 11.47 | 6.84 | 7.41 |
| 4-Cl-F | 13.16 | 4.88 | 2.8 | 4.15 |
| 4-CN-F | 44.24 | 6.27 | 10.01 | 9.46 |
| 4-NO2-F | 27.76 | 12.04 | 3.73 | 5.76 |
| 4-MeO-F | 36.69 | 15.34 | 10.79 | 4.5 |
| 3-NO2-Y | 19.5 | 22.74 | 90.66 | 49.03 |
| Nal | 15.11 | 11.03 | 3.6 | 3.73 |
| Pal | 293.8 | 212.4 | 69.23 | 45.33 |
| Cha | 25.49 | 19.83 | 1.37 | 5.63 |
| CRLLIW | | | 7.7 | 9.6 |

Activity of the molecules improves with a fluorophore attached to the cysteine (in this case FITC-maleimide bound to the cysteine). But this can be extended to any bulky aromatic or aliphatic residue in that position.

Activity as measured by a HIF-2 ELISA is as follows for fluorescently tagged molecule:

FITC-CRLLIF-0.47 μM (SEQ ID NO 3)

FITC-CKLIIF-0.77 μM (SEQ ID NO 2)

FITC-CRVIIF-1.46 μM (SEQ ID NO 4)

The above molecules, or derivatives with non-natural amino acids may be used for the discovery of new HIF-1 and HIF-2 inhibitors using a fluorescence polarization assay.

The invention claimed is:

1. An isolated polypeptide that specifically inhibits or prevents dimerization of HIF-1α (hypoxia inducible factor-1α) with HIF-1β and HIF-2α with HIF-1β and/or inhibits the activity of HIF-1 and/or HIF-2, wherein the polypeptide comprises the amino acid sequence CXZZZF (SEQ ID NO:7);

wherein X is arginine, lysine, or a non-natural derivative of arginine or lysine and Z is leucine, valine, isoleucine, or a non-natural derivative of leucine, valine, or isoleucine, and wherein the polypeptide is a cyclic polypeptide.

2. The polypeptide according to claim 1, wherein the polypeptide consists of the sequence CKLIF (SEQ ID NO: 2), CRLLIF (SEQ ID NO: 3), or CRVIIF (SEQ ID NO: 4).

3. The polypeptide according to claim 1, wherein the polypeptide consists of the sequence CKLIIF (SEQ ID NO: 2).

4. The polypeptide according to claim 1, wherein the polypeptide has a sequence selected from CKLIIF (SEQ ID NO: 2); CRLLIF (SEQ ID NO: 3); and CRVIIF (SEQ ID NO: 4).

5. The polypeptide according to claim 1, wherein one or more of the amino acids is replaced with a D amino acid.

6. The polypeptide according to claim 1, wherein one or more of the amide bonds in the peptide backbone is modified or replaced with an isostere.

7. A pharmaceutical composition comprising the polypeptide according to claim 1.

8. The pharmaceutical composition of claim 7, wherein the pharmaceutical composition further comprises a chemotherapeutic agent.

9. A method of inhibiting activity of HIF-1 and/or HIF-2 in vitro, wherein the method comprises contacting HIF-1 and/or HIF-2 in vitro with the polypeptide according to claim 1.

* * * * *

SEQUENCE LISTING

```
<160> NUMBER OF SEQ ID NOS: 44

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MISC_FEATURE
<222> LOCATION: (5)..(5)
<223> OTHER INFORMATION: X is L, I or V
<220> FEATURE:
<221> NAME/KEY: MISC_FEATURE
<222> LOCATION: (6)..(6)
<223> OTHER INFORMATION: X is any amino acid

<400> SEQUENCE: 1

Cys Xaa Xaa Xaa Xaa Xaa
1               5

<210> SEQ ID NO 2
<211> LENGTH: 6
<212> TYPE: PRT
<213> ORGANISM: Homo sapiens

<400> SEQUENCE: 2

Cys Lys Leu Ile Ile Phe
1               5

<210> SEQ ID NO 3
<211> LENGTH: 6
<212> TYPE: PRT
<213> ORGANISM: Homo sapiens
```

```
<400> SEQUENCE: 3

Cys Arg Leu Leu Ile Phe
1               5

<210> SEQ ID NO 4
<211> LENGTH: 6
<212> TYPE: PRT
<213> ORGANISM: Homo sapiens

<400> SEQUENCE: 4

Cys Arg Val Ile Ile Phe
1               5

<210> SEQ ID NO 5
<211> LENGTH: 9
<212> TYPE: PRT
<213> ORGANISM: Homo sapiens

<400> SEQUENCE: 5

Ser Gly Trp Glu Met Ile Gln Arg Arg
1               5

<210> SEQ ID NO 6
<211> LENGTH: 6
<212> TYPE: PRT
<213> ORGANISM: Homo sapiens
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid

<400> SEQUENCE: 6

Cys Xaa Xaa Xaa Ile Xaa
1               5

<210> SEQ ID NO 7
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is R or K
<220> FEATURE:
<221> NAME/KEY: MISC_FEATURE
<222> LOCATION: (3)..(5)
<223> OTHER INFORMATION: X is L, I or V

<400> SEQUENCE: 7

Cys Xaa Xaa Xaa Xaa Phe
1               5

<210> SEQ ID NO 8
<211> LENGTH: 5
<212> TYPE: PRT
<213> ORGANISM: Homo sapiens

<400> SEQUENCE: 8

Cys Arg Leu Leu Ile
1               5

<210> SEQ ID NO 9
```

```
<211> LENGTH: 6
<212> TYPE: PRT
<213> ORGANISM: Homo sapiens

<400> SEQUENCE: 9

Cys Arg Leu Leu Ile Tyr
1               5

<210> SEQ ID NO 10
<211> LENGTH: 6
<212> TYPE: PRT
<213> ORGANISM: Homo sapiens

<400> SEQUENCE: 10

Cys Arg Leu Leu Ile Trp
1               5

<210> SEQ ID NO 11
<211> LENGTH: 6
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is L, I or V
<220> FEATURE:
<221> NAME/KEY: MISC_FEATURE
<222> LOCATION: (5)..(5)
<223> OTHER INFORMATION: X is any amino acid

<400> SEQUENCE: 11

Xaa Xaa Xaa Xaa Xaa Cys
1               5

<210> SEQ ID NO 12
<211> LENGTH: 6
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is L, I or V
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid

<400> SEQUENCE: 12

Xaa Xaa Xaa Xaa Cys Xaa
1               5

<210> SEQ ID NO 13
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any amino acid
```

```
<220> FEATURE:
<221> NAME/KEY: MISC_FEATURE
<222> LOCATION: (2)..(2)
<223> OTHER INFORMATION: X is any L, I or V
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (5)..(6)
<223> OTHER INFORMATION: X is any amino acid

<400> SEQUENCE: 13

Xaa Xaa Xaa Cys Xaa Xaa
1               5

<210> SEQ ID NO 14
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any L, I or V
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(6)
<223> OTHER INFORMATION: X is any amino acid

<400> SEQUENCE: 14

Xaa Xaa Cys Xaa Xaa Xaa
1               5

<210> SEQ ID NO 15
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any amino acid
<220> FEATURE:
<221> NAME/KEY: MISC_FEATURE
<222> LOCATION: (3)..(5)
<223> OTHER INFORMATION: X is any amino acid
<220> FEATURE:
<221> NAME/KEY: MISC_FEATURE
<222> LOCATION: (6)..(6)
<223> OTHER INFORMATION: X is L, I or V

<400> SEQUENCE: 15

Xaa Cys Xaa Xaa Xaa Xaa
1               5

<210> SEQ ID NO 16
<211> LENGTH: 6
<212> TYPE: PRT
<213> ORGANISM: Homo sapiens

<400> SEQUENCE: 16

Lys Leu Ile Ile Phe Cys
1               5

<210> SEQ ID NO 17
<211> LENGTH: 6
<212> TYPE: PRT
```

```
<213> ORGANISM: Homo sapiens

<400> SEQUENCE: 17

Leu Ile Ile Phe Cys Lys
1               5

<210> SEQ ID NO 18
<211> LENGTH: 6
<212> TYPE: PRT
<213> ORGANISM: Homo sapiens

<400> SEQUENCE: 18

Ile Ile Phe Cys Lys Leu
1               5

<210> SEQ ID NO 19
<211> LENGTH: 6
<212> TYPE: PRT
<213> ORGANISM: Homo sapiens

<400> SEQUENCE: 19

Ile Phe Cys Lys Leu Ile
1               5

<210> SEQ ID NO 20
<211> LENGTH: 6
<212> TYPE: PRT
<213> ORGANISM: Homo sapiens

<400> SEQUENCE: 20

Phe Cys Lys Leu Ile Ile
1               5

<210> SEQ ID NO 21
<211> LENGTH: 6
<212> TYPE: PRT
<213> ORGANISM: Homo sapiens

<400> SEQUENCE: 21

Arg Leu Leu Ile Phe Cys
1               5

<210> SEQ ID NO 22
<211> LENGTH: 6
<212> TYPE: PRT
<213> ORGANISM: Homo sapiens

<400> SEQUENCE: 22

Leu Leu Ile Phe Cys Arg
1               5

<210> SEQ ID NO 23
<211> LENGTH: 6
<212> TYPE: PRT
<213> ORGANISM: Homo sapiens

<400> SEQUENCE: 23

Leu Ile Phe Cys Arg Leu
1               5

<210> SEQ ID NO 24
<211> LENGTH: 6
<212> TYPE: PRT
<213> ORGANISM: Homo sapiens
```

```
<400> SEQUENCE: 24

Ile Phe Cys Arg Leu Leu
1               5

<210> SEQ ID NO 25
<211> LENGTH: 6
<212> TYPE: PRT
<213> ORGANISM: Homo sapiens

<400> SEQUENCE: 25

Phe Cys Arg Leu Leu Ile
1               5

<210> SEQ ID NO 26
<211> LENGTH: 6
<212> TYPE: PRT
<213> ORGANISM: Homo sapiens

<400> SEQUENCE: 26

Arg Val Ile Ile Phe Cys
1               5

<210> SEQ ID NO 27
<211> LENGTH: 6
<212> TYPE: PRT
<213> ORGANISM: Homo sapiens

<400> SEQUENCE: 27

Val Ile Ile Phe Cys Arg
1               5

<210> SEQ ID NO 28
<211> LENGTH: 6
<212> TYPE: PRT
<213> ORGANISM: Homo sapiens

<400> SEQUENCE: 28

Ile Ile Phe Cys Arg Val
1               5

<210> SEQ ID NO 29
<211> LENGTH: 6
<212> TYPE: PRT
<213> ORGANISM: Homo sapiens

<400> SEQUENCE: 29

Ile Phe Cys Arg Val Ile
1               5

<210> SEQ ID NO 30
<211> LENGTH: 6
<212> TYPE: PRT
<213> ORGANISM: Homo sapiens

<400> SEQUENCE: 30

Phe Cys Arg Val Ile Ile
1               5

<210> SEQ ID NO 31
<211> LENGTH: 9
<212> TYPE: PRT
<213> ORGANISM: Homo sapiens

<400> SEQUENCE: 31
```

Gly Trp Glu Met Ile Gln Arg Arg Ser
1               5

<210> SEQ ID NO 32
<211> LENGTH: 9
<212> TYPE: PRT
<213> ORGANISM: Homo sapiens

<400> SEQUENCE: 32

Trp Glu Met Ile Gln Arg Arg Ser Gly
1               5

<210> SEQ ID NO 33
<211> LENGTH: 9
<212> TYPE: PRT
<213> ORGANISM: Homo sapiens

<400> SEQUENCE: 33

Glu Met Ile Gln Arg Arg Ser Gly Trp
1               5

<210> SEQ ID NO 34
<211> LENGTH: 9
<212> TYPE: PRT
<213> ORGANISM: Homo sapiens

<400> SEQUENCE: 34

Met Ile Gln Arg Arg Ser Gly Trp Glu
1               5

<210> SEQ ID NO 35
<211> LENGTH: 9
<212> TYPE: PRT
<213> ORGANISM: Homo sapiens

<400> SEQUENCE: 35

Ile Gln Arg Arg Ser Gly Trp Glu Met
1               5

<210> SEQ ID NO 36
<211> LENGTH: 9
<212> TYPE: PRT
<213> ORGANISM: Homo sapiens

<400> SEQUENCE: 36

Gln Arg Arg Ser Gly Trp Glu Met Ile
1               5

<210> SEQ ID NO 37
<211> LENGTH: 9
<212> TYPE: PRT
<213> ORGANISM: Homo sapiens

<400> SEQUENCE: 37

Arg Arg Ser Gly Trp Glu Met Ile Gln
1               5

<210> SEQ ID NO 38
<211> LENGTH: 9
<212> TYPE: PRT
<213> ORGANISM: Homo sapiens

<400> SEQUENCE: 38

Arg Ser Gly Trp Glu Met Ile Gln Arg
1               5

```
<210> SEQ ID NO 39
<211> LENGTH: 6
<212> TYPE: PRT
<213> ORGANISM: Homo sapiens

<400> SEQUENCE: 39

Ala Arg Val Ile Ile Phe
1               5

<210> SEQ ID NO 40
<211> LENGTH: 6
<212> TYPE: PRT
<213> ORGANISM: Homo sapiens

<400> SEQUENCE: 40

Cys Ala Val Ile Ile Phe
1               5

<210> SEQ ID NO 41
<211> LENGTH: 6
<212> TYPE: PRT
<213> ORGANISM: Homo sapiens

<400> SEQUENCE: 41

Cys Arg Ala Ile Ile Phe
1               5

<210> SEQ ID NO 42
<211> LENGTH: 6
<212> TYPE: PRT
<213> ORGANISM: Homo sapiens

<400> SEQUENCE: 42

Cys Arg Val Ala Ile Phe
1               5

<210> SEQ ID NO 43
<211> LENGTH: 6
<212> TYPE: PRT
<213> ORGANISM: Homo sapiens

<400> SEQUENCE: 43

Cys Arg Val Ile Ala Phe
1               5

<210> SEQ ID NO 44
<211> LENGTH: 6
<212> TYPE: PRT
<213> ORGANISM: Homo sapiens

<400> SEQUENCE: 44

Cys Arg Val Ile Ile Ala
1               5
```